US011020416B2

(12) United States Patent
Ordahl

(10) Patent No.: US 11,020,416 B2
(45) Date of Patent: *Jun. 1, 2021

(54) CANCER CHEMOTHERAPY EMPLOYING HALOGENATED ANALOGS OF THYMIDINE

(71) Applicant: Charles Ordahl, San Francisco, CA (US)

(72) Inventor: Charles Ordahl, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/391,067

(22) Filed: Apr. 22, 2019

(65) Prior Publication Data

US 2019/0247412 A1    Aug. 15, 2019

Related U.S. Application Data

(63) Continuation of application No. 15/063,455, filed on Mar. 7, 2016, now Pat. No. 10,278,983.

(60) Provisional application No. 62/136,343, filed on Mar. 20, 2015.

(51) Int. Cl.
| | |
|---|---|
| *A61K 31/70* | (2006.01) |
| *A01N 43/04* | (2006.01) |
| *A61K 31/7072* | (2006.01) |
| *A61K 31/7068* | (2006.01) |
| *A61K 9/00* | (2006.01) |
| *A61K 47/02* | (2006.01) |
| *A61K 31/7052* | (2006.01) |
| *A61K 31/7056* | (2006.01) |
| *A61K 31/706* | (2006.01) |
| *A61K 31/7064* | (2006.01) |

(52) U.S. Cl.
CPC ........ *A61K 31/7072* (2013.01); *A61K 9/0019* (2013.01); *A61K 31/7068* (2013.01); *A61K 47/02* (2013.01); *A61K 31/706* (2013.01); *A61K 31/7052* (2013.01); *A61K 31/7056* (2013.01); *A61K 31/7064* (2013.01)

(58) Field of Classification Search
None
See application file for complete search history.

(56) References Cited

PUBLICATIONS

Agrawal, M., et al., The Long-term Efficacy and Safety of Fecal Microbiota Transplant for Recurrent, Severe, and Complicated Clostridium difficile Infection in 146 Elderly Individuals. Journal of clinical gastroenterology, 2015, 5 pages.
Austin, W.R., et al., Nucleoside salvage pathway kinases regulate hematopoiesis by linking nucleotide metabolism with replication stress. The Journal of experimental medicine, 2012. 209(12): p. 2215-2228.
Bai, P., Biology of Poly(ADP-Ribose) Polymerases: The Factotums of Cell Maintenance. Molecular cell, 2015. 58(6): p. 947-958.
Bakhle, Y.S. and W.H. Prusoff, The effect of 5-iodo-2'-deoxyuridine and its mono- and triphosphates on some enzymes concerned with the biosynthesis of DNA in cell-free extracts of murine neoplastic cells. Biochimica et biophysica acta, 1969. 174(1): p. 302-308.
Bauer, P.I., et al., Modification of growth related enzymatic pathways and apparent loss of tumorigenicity of ras transformed bovine endothelial cell line by treatment with 5-iodo-6-amino-1,2-benzopyrone (INH2BP). Int. J. Oncology, 1996. 8: p. 239-252.
Beck, S.L., Additional endpoints and overview of a mouse skeletal variant assay for detecting exposure to teratogens. Teratology, 1993. 47(2): p. 147-157.
Calabresi, P., et al., Initial clinical studies with 5-iodo-2'-deoxyuridine. Cancer Res, 1961.21: p. 550-559.
Chang, A.E., et al., A phase I study of intraarterial iododeoxyuridine in patients with colorectal liver metastases. J Clin Oncol, 1989. 7(5): p. 662-668.
Davar, D., et al., Role of PARP inhibitors in cancer biology and therapy. Current medicinal chemistry, 2012. 19(23): p. 3907-3921.
Dutton, R.W. and J.D. Pearce, A survey of the effect of metabolic antagonists on the synthesis of antibody in an in vitro system. Immunology, 1962. 5: p. 414-423.
Ezzeldin, H. and R. Diasio, Dihydropyrimidine dehydrogenase deficiency, a pharmacogenetic syndrome associated with potentially life-threatening toxicity following 5-fluorouracil administration. Clinical colorectal cancer, 2004. 4(3): p. 181-189.
Filetti, S., N.A. Takai, and B. Rapoport, Prevention by nicotinamide of desensitization to thyrotropin stimulation in cultured human thyroid cells. The Journal of biological chemistry, 1981. 256(3): p. 1072-1075.
Gagne, J.P., et al., Proteome-wide identification of poly(ADP-ribose) binding proteins and poly(ADP-ribose)-associated protein complexes. Nucleic acids research, 2008. 36(22): p. 6959-6976.
Gerner, E.W. and F.L. Meyskens, Jr., Polyamines and cancer: old molecules, new understanding. Nature reviews. Cancer, 2004.4(10): p. 781-792.

(Continued)

*Primary Examiner* — Patrick T Lewis
(74) *Attorney, Agent, or Firm* — Law Office of Christopher Peil; Christopher Peil

(57) ABSTRACT

HAT-Pi chemotherapy arrests uncontrolled replication and metastatic migration of neoplastic cells by inhibiting enzymatic activity of poly(ADP-ribose) polymerase 1 (PARP 1) through administration of one or more halogenated analogs of thymidine (HAT). A full HAT-Pi treatment regimen, involving repeated HAT-Pi courses over extended periods (24 weeks), may lead to tumor regression through HAT-Pi-induced neoplastic cell death and disintegration. Pain related to neoplastic disease may be reduced during HAT-Pi treatment and for extended periods thereafter. Myelosuppression is a potentially life-threatening but manageable HAT-Pi toxicity and other HAT-Pi side-effects may be tolerated by most patients. Acquired patient resistance to HAT-Pi has not been observed. HAT-Pi is potentially teratogenic and is restricted to post-reproductive adults with advanced neoplastic disease. Modified HAT-Pi treatment regimens may allow for broader application to treat additional individuals and/or conditions.

20 Claims, 5 Drawing Sheets

(56) References Cited

PUBLICATIONS

Hakala, M.T., Mode of action of 5-bromodeoxyuridine on mammalian cells in culture. J Biol Chem, 1959. 234: p. 3072-3076.

Hegedus, C. and L. Virag, Inputs and outputs of poly(ADP-ribosyl)ation: Relevance to oxidative stress. Redox biology, 2014. 2C: p. 978-982.

Kinsella, T.J., et al., Pharmacology and phase I/II study of continuous intravenous infusions of iododeoxyuridine and hyperfractionated radiotherapy in patients with glioblastoma multiforme. J Clin Oncol, 1988. 6(5): p. 871-879.

Kinsella, T.J. and E. Glatstein, Clinical experience with intravenous radiosensitizers in unresectable sarcomas. Cancer, 1987. 59(5): p. 908-915.

Kirsten, E., et al., Activity assays for poly-ADP ribose polymerase. Methods Mol Biol, 2004. 287: p. 137-149.

Klecker, R.W., Jr., et al., Clinical pharmacology of 5-iodo-2'-deoxyuridine and 5-iodouracil and endogenous pyrimidine modulation. Clinical pharmacology and therapeutics, 1985. 38(1): p. 45-51.

Kohler, G. and C. Milstein, Continuous cultures of fused cells secreting antibody of predefined specificity. Nature, 1975. 256(5517): p. 495-497.

Kolb, B., et al., Embryonic and postnatal injections of bromodeoxyuridine produce age-dependent morphological and behavioral abnormalities. The Journal of neuroscience : the official journal of the Society for Neuroscience, 1999. 19(6): p. 2337-2346.

Kraus, W.L., PARPs and ADP-Ribosylation Come Into Focus. Molecular cell, 2015. 58(6): p. 901.

Kraus, W.L. and M.O. Hottiger, PARP-1 and gene regulation: progress and puzzles. Molecular aspects of medicine, 2013. 34(6): p. 1109-1123.

Kummar, S., et al., First-in-human phase 0 trial of oral 5-iodo-2-pyrimidinone-2-deoxyribose in patients with advanced malignancies. Clinical cancer research : an official journal of the American Association for Cancer Research, 2013. 19(7): p. 1852-1857.

Kun, E., et al., Quantitative correlation between cellular proliferation and nuclear poly (ADP-ribose) polymerase (PARP-1). Int J Mol Med, 2006. 17(2): p. 293-300.

Kun, E., et al., Regulation of the enzymatic catalysis of poly(ADP-ribose) polymerase by dsDNA, polyamines, Mg2+, Ca2+, histones H1 and H3, and ATP. Biochemistry, 2004. 43(1): p. 210-216.

Lehner B. et al., The dark side of BrdU in neural stem cell biology: detrimental effects on cell cycle, differentiation and survival. Cell and tissue research, 2011. 345(3): p. 313-328.

Levkoff, L.H. et al. Bromodeoxyuridine inhibits cancer cell proliferation in vitro and in vivo. Neoplasia, 2008. 10(8): p. 304-816.

Mark, J.B. and P. Calabresi, Regional protection in cancer chemotherapy. II. Preliminary studies with hypogastric artery infusion of thymidine during treatment with 5-iodo-2'-deoxyuridine. Cancer chemotherapy reports. Part 1, 1962. 16: p. 545-551.

Modis, K. et al., Cellular bioenergetics is regulated by PARP1 under resting conditions and during oxidative stress. Biochemical pharmacology, 2012. 83(5): p. 633-643.

Morgan, R.J., Jr., et al., Phase I trial of intraperitoneal iododeoxyuridine with and without intravenous high-dose folinic acid in the treatment of advanced malignancies primarily confined to the peritoneal cavity: flow cytometric and pharmacokinetic analysis. Cancer research, 1998. 58(13): p. 2793-2800.

Mosgoeller, W., et al., Nuclear architecture and ultrastructural distribution of poly(ADP-ribosyl)transferase, a multifunctional enzyme. Journal of cell science, 1996. 109 ( Pt 2): p. 409-418.

Papac, R., et al., Clinical evaluation of the pyrimidine nucleosides 5-fluoro-2'-deoxyuridine and 5-iodo-2'-deoxyuridine. Cancer chemotherapy reports. Part 1, 1962. 20: p. 143-146.

Pivazyan, A.D., et al., Inhibition of poly(ADP-ribose)polymerase activity by nucleoside analogs of thymidine. Biochem Pharmacol, 1992. 44(5): p. 947-953.

Preiss, J., R. Schlaeger, and H. Hilz, Specific inhibition of poly adpribose polymerase by thymidine and nicotinamide in HeLa cells. FEBS Lett, 1971. 19(3): p. 244-246.

Rankin, P.W., et al., Quantitative studies of inhibitors of ADP-ribosylation in vitro and in vivo. J Biol Chem, 1989. 264(8): p. 4312-4317.

Schulz, C.A., et al., Continuous 28-day iododeoxyuridine infusion and hyperfractionated accelerated radiotherapy for malignant glioma: a phase I clinical study. Int J Radiat Oncol Biol Phys, 2004. 59(4): p. 1107-1115.

Schwartz, J.L., Analysis of bromodeoxyuridine-induced single and twin sister chromatid exchanges in tetraploid Chinese hamster ovary cells. Chromosoma, 1986. 93(5): p. 409-412.

Silagi, S. and S.A. Bruce, Suppression of malignancy and differentiation in melanotic melanoma cells. Proc Natl Acad Sci U S A, 1970. 66(1): p. 72-78.

Sumikawa, E., et al., Prolonged unbalanced growth induces cellular senescence markers linked with mechano transduction in normal and tumor cells. Biochemical and biophysical research communications, 2005. 335(2): p. 558-565.

Vyas, S., et al., Family-wide analysis of poly(ADP-ribose) polymerase activity. Nature communications, 2014. 5: 29 pages.

Wilt, F.H., The ontogeny of chick embryo hemoglobin. Proceedings of the National Academy of Sciences of the United States of America, 1962. 48: p. 1582-1590.

Kinsella, et al., Preclinical Evaluation of 5-Iodo-2-pyrimidinone-2'-deoxyribose as a Prodrug for 5-Iodo-2'-deoxyuridine-mediated Radiosensitization in Mouse and Human Tissue, 1998, 12 pages, vol. 4.

Kummar, et al., First-in-Human Phase 0 Trial of Oral-5-Iodo-2-Pyrimidinone-2'-Deoxyribose in Patients with Advanced Malignancies, 2013, 7 pp., vol. 19, No. 7.

Levkoff, et al., Bromodeoxyuridine Inhibits Cancer Cell Proliferation in Vitro and in Vivo, Aug. 2008, 17 pages, vol. 10, No. 8.

Adjuvant Therapy, definition of Adjuvant Therapy by Medical Dictionary, Mosby's Medical Dictionary, 2009, 3 pages.

deoxythymidine iododeoxyuridine bromodeoxyuridine

Circulatory infusion regimen

Peritoneal infusion regimen

Oral tablet regimen (potential)

CANCER CHEMOTHERAPY EMPLOYING HALOGENATED ANALOGS OF THYMIDINE

CROSS REFERENCE TO RELATED APPLICATIONS

This application is a continuation of U.S. patent application Ser. No. 15/063,455, filed on Mar. 7, 2016.

U.S. patent application Ser. No. 15/063,455 claims benefit of U.S. Provisional patent application Ser. No. 62/136,343, filed Mar. 20, 2015, the entireties of which are incorporated herein by this reference thereto.

BACKGROUND

Technical Field

This disclosure relates to the field of chemotherapy treatment of patients having neoplastic disease. In particular, this disclosure relates to chemotherapy employing halogenated analogs of thymidine (abbreviated "HAT").

Background Information

A. Pain

Cancer-related pain, and cancer symptoms broadly, are generally accepted to result from uncontrolled growth and metastasis of neoplastic cells (tumor cells) within the body. The broad consensus on cancer-related pain management is reflected in the information provided on the following websites:
a) www.cancer.gov/publications/patient-education/pain-control.pdf [NCI];
b) www.cancer.org/treatment/treatment-and-side-effects/physical-side-effects/pain.html (Mayo);
c) www.cancer.gov/types/metastatic-cancer [NCI].

In brief, currently accepted methods for treating pain and other symptoms caused by neoplastic cell growth and metastases involve a "3 tier pyramid" in which the medication of last resort is morphine and other synthetic and natural opioid-related drugs which relieve pain through opioid receptor binding in nerve cells that transmit and/or receive pain signals. Patient-acquired resistance limits the long-term effectiveness of morphine and related drugs. In addition, side effects can affect consciousness, normal day-to-day activity, and potentially lead to lethality.

B. Cell-Kill Strategy for Cancer Therapy

It is generally accepted that uncontrolled tumor growth results mainly from uncontrolled replication of neoplastic cells. Currently accepted methods for reducing neoplastic cell replication involve "cell-kill" (cytolytic) agents including but not limited to ionizing radiation and chemotherapy agents that were originally developed in the 1950s many of which persist in present day practice. Because replicating cells are generally considered to be the principal killing targets for such cell-kill methods, the high rate of cell replication in tumors is generally believed to elevate tumor cell-kill rates. Limitations to the extended, long-term use of cell-kill agents are due principally to: (a) debilitating side-effects on non-neoplastic (normal) cells and tissues (including both replicating and non-replicating cells), and; (b) resistance acquired by surviving neoplastic cells to the effects of cell-kill chemotherapy drugs. In some cases, alternative cell-kill drugs, alone or in combination, may be employed to mitigate acquired resistance.

C. Abnormal Neoplastic Cell Behavior

Neoplastic cells share a common set of abnormal cellular behaviors that distinguish them from normal, non-neoplastic cells. The abnormal behavior of neoplastic cells in culture (in vitro) are broadly correlated with the abnormal behavior of tumor cells within the body. Abnormal neoplastic cell behaviors in culture include, but are not limited to:

1. Uncontrolled Neoplastic Cell Replication

Uncontrolled neoplastic cell replication occurs without regard to cell-intrinsic and cell-extrinsic controls that typically govern replication of normal cells in the body's tissues and organs. Uncontrolled neoplastic cell replication is a primary cause of tumor growth. The impingement of uncontrolled tumor growth upon neighboring tissues is a principal cause of cancer-associated pain and other discomfort.

2. Unanchored Neoplastic Cell Survival

Neoplastic cells in culture are able to survive without being anchored (attached) to a substrate, while normal cells typically die, through autonomous mechanisms, if unable to attach to a compatible substrate. Neoplastic cells can also survive and replicate in soft agar where no compatible surface or substrate is available for attachment, a condition in which normal cells cannot survive.

Substrate-attachment and extensive cell-cell attachments and interactions are also the general rule for cells in the tissues of the body except for circulating cells of the blood and lymphatic spaces which are variously adapted to continuous motility.

3. Absence of Contact Inhibited Neoplastic Cell Motility and Replication

Expansion and movement of normal cells in a culture dish are restricted to the plane of the substrate on the dish surface and proceed through extension of membrane filopodia which form complex cell-cell contacts with the surface membranes of neighboring cells.

Such cell-cell contacts result in the inhibition of cell replication among contacted cells. Furthermore, movement of normal cells or their filopodia over the boundaries of neighboring cells rarely occurs.

Neoplastic cells, by contrast, typically pile up on one another in culture dishes due to the absence of contact inhibition and substrate-attachment-dependence. Comparable piling up of cells in culture does not occur with normal (non-neoplastic) cells.

4. Uncontrolled Tumor Growth and Expansion (In Vivo)

It is generally accepted that neoplastic tumor growth is the result of uncontrolled replication of tumor cells that is unconstrained by various cellular mechanisms, including but not limited to, contact inhibition or substrate-attachment-dependence.

5. Metastasis or Spread of Tumor Cells (In Vivo)

It is generally accepted that metastasis, or the spread of malignant tumor cells in the patient body, is dependent upon the movement and migration of neoplastic cells from their site of origin to new sites in the body [www.cancer.gov/types/metastatic-cancer [NCI]. The absence of substrate-attachment-dependence is a neoplastic cell characteristic that is generally believed to permit metastatic cells to survive and replicate during migration.

6. Tumorigenicity (In Vitro and In Vivo)

Tumorigenicity, in general, refers to the ability of tumor cells to expand and colonize new sites in the body of a patient or an experimental animal. It is generally believed that tumorigenicity reflects, to an unquantifiable degree, a summation of the abnormal neoplastic behaviors outlined above.

D. Poly(ADP-Ribose) Polymerase 1 (PARP1)

PARP1[poly(ADP-ribose) polymerase 1(E.C.2.4.2.30)] is a nuclear enzyme that catalyzes the synthesis of the third natural form of nucleic acid, comprising chains of adenosine residues that are oligomeric (2-20 residues) or polymeric (>20 residues) and which are generally collectively referred to here and elsewhere as "poly(ADP-ribose)" (PAR). Initiation of PAR synthesis involves covalent attachment of a single ADP-ribose residue, derived from cleavage of its substrate molecule, $NAD^+$ (nicotinamide adenine dinucleotide, the ubiquitous metabolic coenzyme), to an amino acid residue within a polypeptide chain of a "target" protein. PARP1 is one member of a family of ADP-ribosyltransferase enzymes (ARTS) that share a structurally similar $NAD^+$ (substrate) binding site. Proteins which are trans-modified by PARP1 include but are not limited to histone proteins and regulatory proteins. An enzymatically active PARP1 dimer may also auto-modify by synthesizing a PAR chain attached to one dimer partner. PAR chain elongation involves serial addition of adenine residues derived from $NAD^+$ substrate molecules to generate a linear oligonucleotide chain typically 20 or fewer residues in length but which may be longer and/or branched in some instances. PAR chains are also subject to degradation by another cellular enzyme, Poly (ADP-ribose)glycohydrolase (PARG), which can remove PAR chains from proteins and release 'free' oligomeric PAR chains that are no longer covalently bound to a target protein. Proteins and other macromolecules that bind free PAR chains non-covalently may also be structurally and/or functionally altered in an unknown manner.

Chemotherapy through Inhibition of PARP1 Enzymatic Activity

Clinical trials have employed PARP1 inhibitors to treat neoplastic and other disregulative diseases. Numerous USPTO applications propose, as part of a cancer treatment regimen, the use of one or more PARP1 inhibitors to inhibit repair of DNA strand breaks resulting from either introduced DNA-damage agent(s) or from intrinsic cause(s). A small number of USPTO applications have proposed using PARP1 inhibition-alone for anti-cancer chemotherapy.

PARP1, Molecular Information Link:

www.brenda-enzymes.info use search term "2.4.2.30"

E. Halogenated Analogs of Thymidine (HAT)

1. HAT and HAT-DNA; Definitions

Bromodeoxyuridine and iododeoxyuridine are halogenated analogs of thymidine (HAT) because, in biological systems, each mimics thymidine, a natural metabolite. HAT compounds (and related compounds including, but not limited to, bromouracil and iodouracil) enter human cells and other animal cells by passive and active transport. During cell replication, and other cellular processes involving DNA synthesis, HAT compounds are efficiently incorporated into DNA in place of the natural precursor, thymidine. DNA containing HAT is referred to as "HAT-DNA" in this document.

Due to its ease of incorporation into DNA, and sensitive methods available to detect such incorporation, HAT compounds are in broad use world-wide as markers to detect HAT-DNA in purified systems, as well as in living cells, tissues and organs.

2. HAT Anti-Neoplastic Effects Widely Attributed to HAT-DNA

Anti-neoplastic effects result when HAT compounds are added to the culture medium of a wide variety of cultured neoplastic cells. HAT anti-neoplastic effects on neoplastic cells include but are not limited to:

a. arrest of uncontrolled neoplastic cell replication;

b. neoplastic cell-survival becoming anchorage-dependent; and c. neoplastic cell death and disintegration after HAT exposure for extended periods.

These and other anti-neoplastic effects of HAT that have been observed in cultures of neoplastic cells have been widely and generally attributed to HAT-DNA despite the absence of any generally accepted evidence or hypothesis that explains how HAT-DNA might exert any such anti-neoplastic effect including, but not limited to, those outlined above.

3. HAT-DNA and Adjuvant Therapy

HAT compounds have also been widely employed as adjuvants intended to increase cell-sensitivity to the DNA-damaging effects of radiation therapy and/or by DNA-damaging drug chemotherapy. Such usage is based upon the generally accepted rationale that the DNA in neoplastic tumor cells is more easily broken during therapy with DNA damage agents (radiotherapy and/or chemotherapy) when some or all thymidine nucleotide positions in their DNA are occupied by HAT nucleotides (HAT-DNA).

4. HAT-DNA: The Sole Cellular Target of Current HAT-Based Chemotherapy Methods

In conclusion, in all current antineoplastic concepts, explanations and applications of HAT chemotherapy, DNA is the exclusive cellular molecule targeted and all therapeutic uses are based solely on the central concept that the presence of HAT nucleotides in neoplastic cell DNA alters its physical and biological properties in a manner that has antineoplastic effects for therapeutic purposes.

The term "HAT-DNA", as used in this document, refers specifically to DNA molecules that have incorporated bromodeoxyuridine and/or iododeoxyuridine nucleotides in place of thymidine nucleotides either partially or completely. This term is also used more broadly to describe, distinguish or identify ideas, hypotheses, treatments and/or therapies that are based upon HAT-DNA ideation, concept, or model.

SUMMARY

HAT-Pi chemotherapy arrests uncontrolled replication and metastatic migration of neoplastic cells by inhibiting enzymatic activity of poly(ADP-ribose) polymerase 1 (PARP 1) through administration of one or more halogenated analogs of thymidine (HAT). A full HAT-Pi treatment regimen, involving repeated HAT-Pi courses over extended periods (24 weeks), may lead to tumor regression through HAT-Pi-induced neoplastic cell death and disintegration. Pain related to neoplastic disease may be reduced during HAT-Pi treatment and for extended periods thereafter. Myelosuppression is a potentially life-threatening but manageable HAT-Pi toxicity and other HAT-Pi side-effects may be tolerated by most patients. Acquired patient resistance to HAT-Pi has not been observed. HAT-Pi is potentially teratogenic and is restricted to post-reproductive adults with advanced neoplastic disease. Modified HAT-Pi treatment regimens may allow for broader application to treat additional individuals and/or conditions.

DETAILED DESCRIPTION

Introduction

Figure 1:
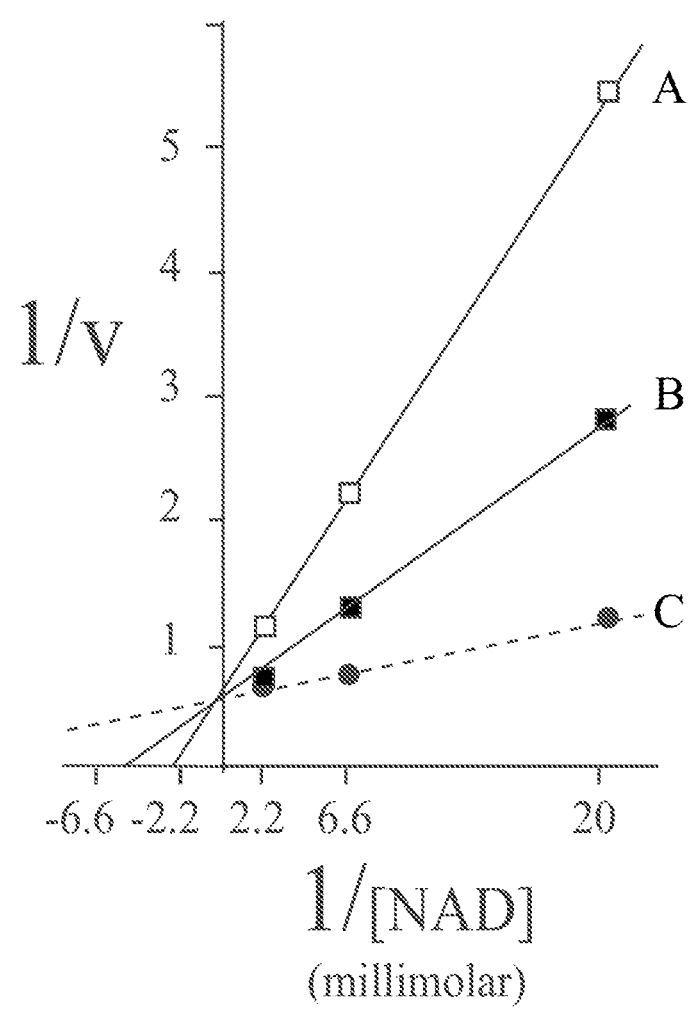
FIG. 1 provides a graph illustrating HAT inhibition of PARP-1 enzymatic activity (HAT-Pi)

HAT-Pi chemotherapy arrests uncontrolled replication and metastatic migration of neoplastic cells by inhibiting enzymatic activity of poly(ADP-ribose) polymerase 1 (PARP 1) through administration of one or more halogenated analogs of thymidine (HAT). A full HAT-Pi treatment regimen, involving repeated HAT-Pi courses over extended periods (24 weeks), may lead to tumor regression through HAT-Pi-induced neoplastic cell death and disintegration. Pain related to neoplastic disease may be reduced during HAT-Pi treatment and for extended periods thereafter. Myelosuppression is a potentially life-threatening but manageable HAT-Pi toxicity and other HAT-Pi side-effects may be tolerated by most patients. Acquired patient resistance to HAT-Pi has not been observed. HAT-Pi is potentially teratogenic and is restricted to post-reproductive adults with advanced neoplastic disease. Modified HAT-Pi treatment regimens may allow for broader application to treat additional individuals and/or conditions.

I. Unexpected Discoveries Lead to Invention of HAT-Pi Chemotherapy.

The discoveries leading to invention of HAT-Pi chemotherapy arose from analysis and re-evaluation of scientific studies published in peer-reviewed journals and from unpublished results. The discoveries are "unexpected" because the following propositions are new and first publicly presented here. Briefly these discoveries lead to the following conclusions:

1. HAT anti-neoplastic effects on neoplastic cells in culture are exerted through concentration-dependent, competitive inhibition of PARP1 enzymatic activity, and not by HAT-DNA (i.e. the substitution of HAT nucleotides for thymidine in neoplastic cell DNA molecules). Therefore, the primary target of HAT-Pi chemotherapy is inhibition of PARP1 enzymatic activity (Pi) and not HAT-DNA as in all previous applications.

2. Historic HAT-Pi Patients (*) experienced anti-tumorigenic effects including, but not limited to, reduction in pain and tumor regression, accompanied by minimal and manageable side effects (*Historic HAT-Pi patients were infused with HAT for extended periods and experienced plasma HAT concentrations in excess of 1.0 micromolar, a concentration expected to partially or completely inhibit PARP1 enzymatic activity intracellularly.)

3. HAT-Pi chemotherapy is cytostatic, meaning that it results in the arrest of uncontrolled behaviors of neoplastic cells,—specifically; inhibition of uncontrolled neoplastic cell replication and uncontrolled neoplastic cell movements—that are associated with uncontrolled tumor growth and metastases of neoplastic tumor cells within the body.

4. A regimen of HAT-Pi chemotherapy may lead to measurable tumor regression as HAT-Pi-arrested neoplastic cells undergo cell disintegration and cell death through neoplastic cell-autonomous processes.

5. A regimen of HAT-Pi may not irreversibly cure neoplastic disease because HAT-Pi, and the anti-neoplastic effects of HAT-Pi, are potentially reversible in any or all surviving neoplastic tumor cells. Additional rounds of HAT-Pi may be applied to prevent or diminish the resumption of unregulated growth and metastases by remaining neoplastic cells.

Because of these attributes, HAT-Pi chemotherapy has the potential to serve as:

a. an alternative to conventional cell-kill chemotherapy or radiotherapy options.

b. a follow-up chemotherapy option for patients after conventional chemotherapy or radiotherapy options have been exhausted or are no longer deemed suitable.

c. a palliative treatment to prevent or delay employment of opioid-type pain medications.

The following exposition of the discoveries leading to the present invention is based on scientific and clinical reports published in peer-reviewed journals from multiple fields over several decades and on experimental studies reported herein. Its organization is not chronological.

A. PARP1 Enzymatic Activity

PARP1 enzymatic activity is generally low in normal cells and tissues despite the abundance of PARP1 protein in the cell nucleus, consistent with the conclusion that the activity of this enzyme is normally subject to stringent physiological regulation. Analysis of purified human PARP1 enzymatic reaction kinetics using physiological conditions combined with classical enzyme analytical methods has identified physiological activators and inhibitors of PARP1 activity (E. Kun, E. Kirsten, J. Mendeleyev, and C. P. Ordahl, Biochemistry 43 210 (2004); and references therein; and unpublished observations).

1. Recently Discovered Characteristics of PARP1 Enzymatic Activity a) Intact Chromosomal DNA can Serve as Coenzyme for PARP1 Enzymatic Activity PARP 1 avidly binds to double-stranded DNA and that binding alone can act as a necessary coenzyme for PARP1 to conduct enzymatic activity. In other words, despite the widespread assumption that strand breaks in coenzymic DNA are necessary for PARP1 enzymatic activity in solution, and, in living cells, neither naturally-occurring nor induced DNA strand breaks are required for PARP1 enzymatic activity to be activated or for overall levels of PARP1 enzymatic activity to be elevated. In summary, the double stranded chromosomal DNA present within intact, undamaged cells is a constantly-available and sufficient coenzyme for PARP1 enzymatic activity.

b) PARP1 Auto-Modification is Regulated Differently from Trans-Modification

PARP1 synthesizes ADP-ribose oligomers/polymers in either one of two alternative modes referred to as "auto-modification" and "trans-modification." Auto-modification occurs when one subunit in an enzymatically active PARP1 dimer attaches an ADP-ribose oligomers/polymer to its partner subunit. In trans-modification, an enzymatically active PARP1 dimer attaches ADP-ribose oligomers/polymers to other proteins, including basic proteins such as histones and acidic proteins, such as transcriptional regulatory proteins. In most normal cells and tissues, trans-modification is the predominant activity of PARP1 while PARP1 auto-modification activity is comparatively lower. Cellular controls that govern the switching between auto- and trans-modification activities of PARP1 in living cells include, but are not limited to, the selective inhibition of PARP1 auto-modification by adenosine triphosphate (ATP). PARP1 trans-modification is not affected by ATP.

2. PARP1 Enzymatic Activity is Elevated in Neoplastic Cells.

PARP1 enzymatic activity is elevated in neoplastic cells (E. Kun, E. Kirsten, P. I. Bauer and C. P. Ordahl, International Journal of Molecular Medicine 17 293 (2006); and references therein). Because that elevated level of PARP1 enzymatic activity exists in absence of the introduction of DNA strand breaks by radiation or chemical agents, it must be due to cause(s) and affect cellular function(s) other than DNA repair. Elevated levels of PARP1 enzymatic activity in neoplastic cells are primarily attributable to increased PARP1 auto-modification. Accordingly, auto-modified PARP1 accumulates to become the most abundant among the poly(ADP-ribose)-modified proteins present in neoplastic cells.

The increased PARP1 auto-modification activity in neoplastic cells is a harbinger of the disregulation of endogenous PARP1 enzyme molecules in neoplastic cells. Potential explanations for the increased auto-modification in neoplastic cells include, but are not limited to:

a) Anaerobic Metabolism in Neoplastic Cells.

Anaerobic (glycolytic) metabolism is a distinctive characteristic of neoplastic cells and is less efficient at generating ATP than aerobic metabolism. The ATP concentrations generated within normal cells by oxidative metabolism are sufficient to selectively inhibit PARP1 auto-modification while leaving trans-modification unaffected. The impaired ATP-generating capacity of neoplastic cells, therefore, is partial explanation for dis-inhibition of PARP1 auto-modification activity. Such dis-inhibition of PARP1 auto-modification consumes $NAD^+$, the main cellular molecule responsible for carrying the hydrogen atoms for oxidative metabolism in the mitochondria, thereby further impairing ATP production. A downward spiral may ensue as diminishing ATP levels further dis-inhibit PARP1 auto-modification activity which, in turn, consumes more of the $NAD^+$ molecules removing these essential links to oxidative metabolism which is necessary to efficiently produce new ATP molecules.

The clear metabolic relationships between PARP1 enzymatic activity and $NAD^+$ have already led to proposals that inhibition of PARP1 enzymatic activity may be effective to treat other dis-regulative diseases, including but not limited to mitochondrial diseases and oxidative stress (P. Bai, Molecular Cell 58 947 (2015); and references therein) which may affect multiple organs and tissues. The central roles of $NAD^+$ and ATP in the downward spiral outlined above represent new conceptual elements of HAT-Pi treatment that further underscore and clarify the important relationships between PARP1 dis-regulation and metabolic dis-regulation in cancer and other diseases.

b) Elevated Spermine Levels in Neoplastic Cells

Elevated levels of spermine is a common feature of neoplastic cells that is generally attributed to increased activity of ornithine decarboxylase (ODC), an enzyme which is characteristically elevated in neoplastic cells (E. W. Gerner and F. L. Meyskins, Jr., Nature Reviews Cancer 4 781 (2004); and references therein). Spermine specifically stimulates PARP1 auto-modification but spermine does not stimulate trans-modification of other proteins, such as histones.

c) Elevated PARP1 may be an Indicator of Metabolic Disregulation

The increased PARP1 auto-modification activity in neoplastic cells serves an indicator of the disregulation of endogenous PARP1 enzyme molecules in neoplastic cells for reasons, in part, attributable to the factors outlined above, and possibly to other factors not yet identified (see W. L. Kraus, Molecular Cell 58 901 (2015) and references therein for non-limiting examples).

3. Inhibition of PARP1 Enzymatic Activity in Neoplastic Cells.

a) PARP1 Inhibition Reverses Abnormal Behavior of Neoplastic Cells in Culture

Neoplastic cells cultured in the presence of PARP1 inhibitors spread out on the surface of the culture dish and adopt a flat morphology, indicating that they have become strongly substrate-adherent. In addition, adjacent neoplastic cells form boundaries at cell-cell contact points and do not grow on top of one another, indicating that cell replication and motility is governed by contact inhibition (P. I. Bauer, E. Kirsten, L. J. T. Young, G. Varadi, E. Csonka, K. G. Buki, G. Mikala, R. Hu, J. A. Comstock, J. Mendeleyev, A. Hakam, E. Kun, International Journal of Oncology 8 239 (1996); and references therein). Substrate adherence, contact inhibition and formation of cell-cell contacts are normal cell behaviors which, being universally absent in neoplastic cells, are permissive to abnormal neoplastic cell behaviors that contribute to tumorigenic potential.

b) Extended PARP1 Inhibition can Irreversibly Inhibit Tumorigenic Potential.

The inhibition of neoplastic cell abnormal behavior in culture by PARP1 inhibitors is, initially, reversible but the abnormal behavior and tumorigenic potential of neoplastic cells may be lost in cases where PARP1 inhibition is maintained for extended periods. (P. I. Bauer et al., 1996 op cit; and references therein).

c) Summary; Effects of PARP1 Inhibition (Pi) on Neoplastic Cells in Culture/Prior Art

| neoplastic characteristic | observed Pi effect | technical correlates |
|---|---|---|
| a) unregulated neoplastic cell replication | cell cycle arrest | cytostasis |
| b) abnormal neoplastic cell morphology | cell adhesion/flattening | substrate attachment |
| c) unregulated neoplastic cell motility | regulated motility | contact inhibition |
| d) neoplastic cell viability | cell disintegration (>10 d) | apoptosis |
| e) tumorigenicity of neoplastic cells | lost (>3-7 weeks) | in vivo assay |
| f) neoplastic cell metabolism: | 'normal' metabolism | ox/phos restored |

B. HAT Inhibits PARP 1 Enzyme Activity (FIG. 1)

1. HAT Inhibits Enzymatic Activity of Human PARP1 in Solution.

Michaelis-Menten kinetic analysis of human PARP1 enzymatic activity in solution (aka "in vitro"), and including use of physiological conditions as outlined above, was used to compare the enzymatic activity of PARP1 alone (in the absence of any inhibitors) and in the presence of; a) 3-amino-benzamide, a prototypic PARP1 inhibitor; and b) bromodeoxyuridine, a HAT.

The results of that comparison are illustrated in the Lineweaver-Burk plot shown in FIG. 1. PARP1 enzymatic activity in the absence of any inhibitor (control) is shown by line C in FIG. 1. Lines A and B show the activity in the presence of 3-amino-benzamide and HAT, respectively. Lines A and B intersect the vertical axis at the same point as the no-inhibitor control line (C), indicating that both inhibitors act through binding to the enzyme active site in competition with the substrate, $NAD^+$.

The steepness of the lines in FIG. 1 is proportional to binding strength and shows that 3-amino-benzamide (line A) binds PARP1 more avidly than does bromodeoxyuridine (line B). The intercept at the horizontal axis indicates an inhibition constant for 3-amino-benzamide that is at or below 10 micromolar in general agreement with literature values. The bromodeoxyuridine inhibitory constant may be in the low micromolar range (approximately 10-30 micromolar).

In conclusion HAT is an inhibitor of PARP1 enzymatic activity with inhibitory strength in solution approaching that of known strong PARP1 inhibitors.

2. Prior Reports of PARP1 Inhibition by HAT:

Experimental demonstration of inhibition of PARP1 enzymatic activity by HAT compounds has been reported several times over the past several decades.

| HAT* | Citation | PARP1 activity analyzed in | reported HAT inhibitory effect |
|---|---|---|---|
| B | Preiss, 1971 | isolated HeLa cell nuclei | 1 mM = 97% inhibition |
| B | Filetti, 1981 | cultured human thyroid cells | 50 mM blocks hormone sensitization |
| B | Rankin, 1989 | solution/cultured $10T_{1/2}$ cells | $IC_{50}$ = 15/57 micromolar, respectively |
| B & I | Pivazyan, 1992 | solution | $K_i$ = 18/35 micromolar (I/B) |

*HAT abbreviations: B, bromodeoxuridine; I, iododeoxyuridine.

Full Citations for Above List

J. Preiss, R. Schlaeger, H. Hilz, FEBS LETTERS 19 244 (1971).

S. Filetti, N. A. Takai, B. Rapoport, Journal of Biological Chemistry 256 1072 (1981).

P. W. Rankin, E. L. Jacobson, R. C. Benjamin, J. Moss, M. K. Jacobson, Journal of Biological Chemistry 264 4312 (1989).

A. D. Pivazyan, E. M. Birks, T. G. Wood, T. S. Lin, W. H. Prusoff, Biochemical Pharmacology 33 947 (1992).

These prior studies may have underestimated the strength of HAT inhibition of PARP1 due to non-physiological assay conditions including, but not limited to, usage of broken DNA as coenzyme, and lacking information obtainable only by kinetic analysis employing classical Michaelis-Menten methods.

3. Relative Strength of HAT Inhibition of PARP1

Direct comparison in vitro of PARP1 inhibition strength (Pivazyan 1992, op cit, see above) indicates that iododeoxyuridine has higher avidity for PARP1, as compared to bromodeoxyuridine, and therefore may be considered to be the stronger of the two as an inhibitor of PARP1 activity.

C. HAT-Induced Anti-Neoplastic Effects in Cell Culture (FIG. 2)

FIG. 1 shows that PARP1 enzymatic activity is inhibited in solution by low micromolar concentrations of either 3-aminobenzamide or HAT. In culture, 10 micromolar HAT in the medium may be sufficient to inhibit PARP1 enzymatic activity intracellularly because HAT molecules, as thymidine analogs, freely enter neoplastic cells and thereby inhibit abnormal neoplastic cell behavior.

1. HAT Uptake by Cells

HAT is passively transported across the plasmalemma, or outer cell membrane, to gain entry into the cytoplasm and ultimately into the nucleoplasm and mitochondria, cell sites where PARP1 enzymatic activity is known to occur. With 10 micromolar HAT in the culture medium, passive diffusion of HAT across the cell membrane leads to intracellular HAT concentrations that approach 10 micromolar. HAT is actively transported across the cell membrane in cells engaged in DNA synthesis (S-phase cells), and intracellular HAT concentrations may exceed the extracellular concentration in such cells.

2. HAT-Induced Changes in Cultured Neoplastic Cell Morphology and Behavior

Neoplastic cells in culture that are exposed to 10 micromolar HAT undergo a distinctive set of alterations in their appearance (morphology; cell-shape characteristics) and behavior that reflect the effects of inhibition of PARP1 enzymatic activity. FIGS. 2A-D illustrate HAT-Pi effects on two neoplastic cell lines; a) Calu-6, a human lung carcinoma cell line; and, b) DU-145, a human prostate metastatic carcinoma cell line.

The cell-outline tracings in FIGS. 2A-D illustrate the microscopic appearance of these two neoplastic cell types after being cultured for 14 days without drug (Panels A and C) or after culture for 14 days in medium containing 10 micromolar HAT (Panels B and D).

Neoplastic Cells Cultured without HAT

Tracings of the outlines of individual Calu-6 cells (FIG. 2A) and DU-145 cells (FIG. 2C) illustrate the distinctive and characteristic morphologies of these two neoplastic cell types; Calu6 cells appear "spindle-shaped" while DU-145 cells appear more "rounded". The individual cells are small in both cultures, each consisting of one or more nuclei surrounded by thin layer of cytoplasm. Both cultures are densely crowded with multi-layered masses of small cells packed tightly together (more than 300 cells in each frame). Taken together, these morphological characteristics reflect the absence of contact inhibition and substrate-attachment-dependence, both characteristic behaviors of normal (non-neoplastic) cells.

To summarize, two human neoplastic cell lines cultured in plain medium for 14 days exhibit characteristic morphology and appearances that are typical of cultured neoplastic cells in general and which are consistent with lack of substrate-attachment-dependence and contact inhibition. These characteristic features include, but are not limited to:

a. large numbers of cells filling the field of view due to uncontrolled cell replication;

b. extreme cell crowding, cells have grown on top of one another and are not adherent to dish surface;

c. small cell size, consisting mostly of one or more nuclei but with little cytoplasm;

d. indistinct cell boundaries due to absence of functioning cell-cell contact/communication; and e. absence of evidence of contact inhibition.

These abnormal characteristics of neoplastic cells in culture are related to the uncontrolled neoplastic cell replication and the metastatic motility of neoplastic tumor cells in a body.

Neoplastic Cells Cultured with Low Micromolar HAT (Right-Hand Panels)

Profound changes in the morphology of Calu-6 cells (FIG. 2B) and DU-145 cells (FIG. 2D) can be observed after 14 days in culture in the presence of HAT (10 micromolar bromodeoxyuridine). Most importantly, the total number of cells is substantially reduced (fewer than 50 cells per field), with cell losses being attributable to cell disintegration and death. Additionally, the overall appearance of the cultures and the morphology of the surviving cells is altered in specific ways. First, the remaining (surviving) cells are tightly adherent to the surface of the culture dish giving them a "flattened" appearance. Second, neoplastic cell expansion is attributable to cytoplasmic growth, which leaves the smaller internal cell nuclei distinctive in outline. Third, many cell outlines are "ruffled" in some regions due to the presence of lamellipodia, plasmalemma projections that are the leading edges of cell expansion (open arrows in FIGS. 2B and 2D). Fourth, specialized cell-cell contact and communication regions are evident where the lamellipodia of two or more cells meet (closed arrows in FIGS. 2B and 2D). Fifth, lamellipodia expansion is restricted to bare areas on the culture dish surface, indicating that HAT-treated neoplastic cells do not expand over the tops of neighboring cells. These characteristic features of HAT-treated neoplastic cells indicate that substrate-attachment-dependent survival and contact inhibition have both been restored in surviving neoplastic cells.

To summarize, the HAT-induced changes in neoplastic cell cultures include, but are not limited to:

a. substantial diminution in cell numbers due to cell losses including disintegration and death;
b. cytoplasm expansion giving rise to clear and distinct individual cell boundary outlines and internal outlines of cell nuclei;
c. flattened cells indicating strong substrate-adherence;
d. cell spreading proceeds by well-defined lamellipodia which also adhere to substrate;
e. cell-cell membrane interfaces form at contact points of lamellipodia with neighboring cells; and
f. evident contact inhibition limits cell replication, cell crowding and cell movements.

Importantly, after undergoing the morphological and behavioral changes outlined above, the HAT-treated lung and prostate cancer cells appear more similar to one another than they did prior to HAT treatment, and characteristically similar to many neoplastic cell types after culture in the presence of low micromolar concentrations of HAT (see, as non-limiting examples; M. T. Hakala, Journal of Biological Chemistry 234 3072 (1959); S. Silagi and S. A. Bruce, Proceedings of the National Academy of Sciences (USA) 66 72 (1970); L. H. Levkoff, G. P. Marshall, H. H. Ross, M. Caldeira, B. A. Reynolds, M. Cakiroglu, C. L. Mariani, W. J. Streit, E. D. Laywell, Neoplasia 10 804 (2008); and references therein). Importantly, the HAT-induced characteristics of neoplastic cells also closely resemble common culture characteristics of non-neoplastic cells which may be only amplified with HAT, such as increased cell adhesion. In other words, HAT-treated neoplastic cells cease tumorigenic cell behavior and restore normal cell behavior in culture including, but not limited to, substrate-adherence-dependent cell survival and contact inhibition of cell replication and movement.

Cell senescence, disintegration and death have been reported for neoplastic cell cultures continuously exposed to low micromolar HAT (Levkoff 2008 op cit & references therein) and this is likely to contribute to the reduction in neoplastic cell numbers in HAT-treated cultures.

3. Neoplastic Cell Behaviors Equivalently Inhibited by HAT and known PARP1 Inhibitors The characteristic changes in cultured neoplastic cell appearance and behavior that are induced by HAT treatment (arrest of cell replication and movement accompanied by increased cell adhesion, spreading, and flattening) are similar or identical to those induced by other PARP1 inhibitors, as outlined above.

Importantly, because HAT-inhibits abnormal behaviors which are universal among neoplastic cells (i.e. uncontrolled replication, attachment-independent survival, lack of contact inhibition), it may be inferred that HAT treatment disrupts foundational determinants of the neoplastic state or tumorigenic phenotype and, therefore by extension, HAT treatment has potential to be applicable to many if not all types of neoplasia.

4. Summary of HAT-Induced Anti-Neoplastic Effects In Vitro

| neoplastic characteristic | observed HAT-effect | technical correlates |
| --- | --- | --- |
| a) unregulated neoplastic cell replication: | cell cycle arrest | cytostasis |
| b) abnormal neoplastic cell morphology: | cell adhesion/flattening | substrate attachment |
| c) unregulated neoplastic cell motility | regulated motility | contact inhibition |
| d) neoplastic cell viability: | cell disintegration (>14 d) | apoptosis |
| e) tumorigenicity neoplastic cell: | lost (multiple weeks) | in vivo assay |

D. HAT: Retrospective Analysis of Anti-Neoplastic Effects in Patients (FIG. 3)

1. Historic HAT-Pi Patients: Published Clinical Trial Records

HAT as DNA-Precursor Drug in Patients

HAT (iododeoxyuridine and bromodeoxyuridine) has been administered to hundreds of human patients in NCI-sponsored trials over the past 50+ years. In every one of those trials, HAT was administered as DNA precursor which was intended to replace thymidine residues in neoplastic cell DNA. In some trials, HAT was given to patients based on the hypothesis that HAT-DNA is more readily damaged by radiation or other DNA-damaging agent. In those cases, the effects of HAT on human neoplastic disease may have been partially obscured by the action of the primary, DNA damage agent(s) for many reasons including, but not limited to: (a) DNA damage from the primary agent markedly induces PARP1 enzymatic activity and, thereby, increasing inhibitory load; and (b) PARP1-inhibition may increase tumorigenicity of known carcinogens, including radiation and chemotherapy, potentially creating new neoplastic cells. Moreover, when administered as an adjuvant, the duration of HAT exposure is typically too brief to observe any of the effects of HAT exposure over extended periods. In other words, only a small minority of the patients that have received HAT as a drug were treated under conditions compatible with HAT-Pi, as it is defined here. The defining characteristics of this select group of "historic HAT-Pi patients" are itemized below.

Historic HAT-Pi Patient; a Definition

An historic HAT-Pi patient, for the purposes of this document, is a patient having advanced neoplastic disease reported to have been administered HAT in a published clinical trial:

a) at dosages that achieved HAT plasma concentrations of one (1.0) micromolar, or greater, which are sufficient to partially or completely inhibit intracellular PARP1 enzymatic activity;

b) received "a" chronically for extended periods, (ideally) over multiple weeks or months; and c) received HAT-only, (ideally) without radiation or other DNA damaging agents.

Based upon the anti-neoplastic effects of HAT and other PARP1 inhibitors on neoplastic cells in culture (as outlined above), the antineoplastic effects expected in historic HAT-Pi patients should be evident as improvement in:

Objective Signs;

Objective improvement signs include, but are not limited to, tumor regression (shrinkage in tumor size) and/or reduction in metastases.

Subjective Symptoms;

Symptom improvements include, but are not limited to, reduction of pain and discomfort. Subjective symptoms assessment may comprise patient self-reports and objective measures such as patient use of analgesic and opioid medications.

2. Historic HAT-Pi Patients

HAT-Alone Patients

Genuine historic HAT-Pi patients even constitute a small minority among the subset of patients that received HAT-only because many HAT-only patients received small and/or one-time doses that were intended to assess pharmacology and acute toxicity but lacked therapeutic potential.

Historic HAT-Pi Patients

The small number of trials which had patients who were administered HAT (iododeoxyuridine in each case) at the dosages and durations compatible with HAT-Pi shown in Table 1.

The neoplastic diseases treated in historic HAT-Pi patients and trial citations are listed below.

Trial a. Melanoma, Carcinoma, Sarcoma;
 P. Calabresi, S. S. Cardoso, S. C. Finch, M. M. Kligerman, C. F. Von Essen, M. Y. Chu, A. D. Welch, Cancer Research 21 550 (1961) and references therein.

Trial b. Oropharynx and Upper Extremity Tumors;
 J. B. Mark and P. Calabresi, Cancer Chemotherapy Reports. Part 1 16 545 (1962).

Trial c. Carcinoma, Melanoma;
 R. Papac, E. Jacobs, F. Wong, A. Collom, W. Skoog, D. A. Wood, Cancer Chemotherapy Reports. Part 1 20 143 (1962).

Trial d. Unresectable Sarcoma;
 T J. Kinsella and E. Glatstein, Cancer 59 908 (1987) and references therein.

Trial e. Unresectable Sarcoma;
 Kinsella & Glatstein, 1987 op cit.

Trial f. Colorectal Liver Metastases;
 A. E. Chang, J. M. Collins, P. A. Speth, R. Smith, J. B. Rowland, L. Walton, M. G. Begley, E. Glatstein, T. J. Kinsella, Journal of Clinical Oncolcogy 7 662 (1989) and references therein.

4. Objective Improvement in Historic HAT-Pi Patients

Objective improvement for historic HAT-Pi patients was reported in every study listed in Table 1 and, although specific criteria for assessing objective improvement differed from study-to-study, each included reduction in tumor size and/or tumor growth rate.

The experience of historic HAT-Pi Patient One, discussed below, also illustrates that objective improvement may be variable within an individual patient because some tumor masses at some sites may regress while tumor masses at other sites may not.

5. Subjective/Symptom Improvement in Historic HAT-Pi Patients

Symptom improvement or pain relief is a primary goal of HAT-Pi therapy for advanced neoplastic disease. That goal is based upon published reports of symptom relief for a small number of patients because published studies rarely report on patient symptom response. In those few cases, pain and other symptoms were reduced in some or all patients receiving HAT-Pi therapy (see Table 1).

Symptom/pain-relief was experienced by more than half of patients in one historic HAT-Pi study (Table 1f) in which

TABLE 1

Historic HAT-Pi human patient trials

| trial | year | Pt# | HAT | Dose* | route | HAT dose rad cycle repetitions | objective | subjective |
|---|---|---|---|---|---|---|---|---|
| a | 1961 | 16 | IUDR | 3.1 | iv | +/− Multiple cycles, up to 5 months | 38% | 38% |
| b | 1962 | 4 | IUDR | 3.9 | Iv/ia | − Single cycle, 1 week | 100% | 100% |
| c | 1962 | 39 | IUDR | 3.5 | iv | − Single cycle, 1 week | 26% | NR |
| d | 1987 | 14 | IUDR | 1.3 | iv | + Multiple cycles, up to 5 months | 80% | 57% |
| e | 1987 | 5 | BUDR | 1.3 | iv | + Multiple cycles, up to 5 months | 20% | 20% |
| f | 1989 | 11 | IUDR | 1.0 | ia | − Multiple cycles, up to 5 months | 45% | NR |

NR = not reported

*Doses shown are maximum doses or maximum tolerated doses. Plasma levels of iododeoxyuridine in excess of 1.0 micromolar were demonstrated for dosages indicated in trials d-f. Similar or higher plasma levels are predicted for the dosages indicated for trials a-c.

radiation treatments were also administered during periods between courses of iododeoxyuridine administration. Some of those patients experienced "complete relief of symptoms for the duration of their lives." A subsequent study published two years later by the same team (Table 1e) and with iododeoxyuridine-alone (i.e. without radiation), reported that almost half of the patients received "objective" benefit but did not report any information at all about symptom/pain relief in subject patients. It may be reasonable, however, to assume that patients in the HAT-Pi study with iododeoxyuridine-alone (Table 1e) also experienced relief of symptoms/ pain in proportions at least comparable to those that received radiation and iododeoxyuridine (Table 1f). In fact, without radiation, pain relief from HAT-Pi therapy may improve substantially due to many factors including, but not limited to, the absence of: (a) induced damage to non-neoplastic cells and tissues from the effects of ionizing radiation; and, (b) induced DNA strand breaks which may activate PARP1 enzymatic activity and, therefore, increase the number of active PARP1 enzyme molecules in neoplastic cells which are HAT-Pi targets.

6. Historic HAT-Pi Treatment Regimens

Two representative historic HAT-Pi treatment regimens from the studies itemized in Table 1 are illustrated in FIG. 3 and discussed below.

Figure 3A:
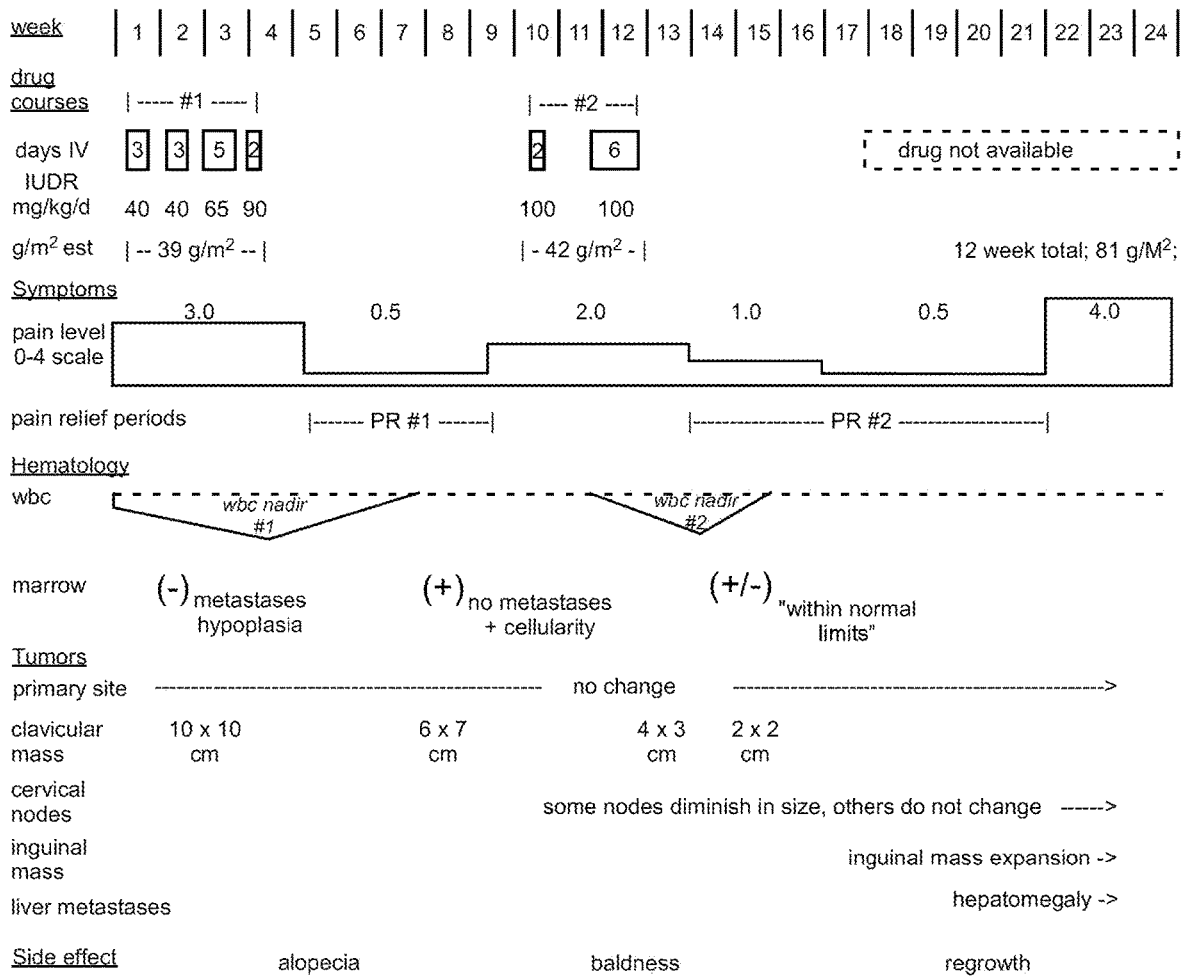
FIGS. 3 A-B provide diagrams illustrating published HAT-Pi treatment regimens.

FIG. 3A: 1st Historic HAT-Pi Regimen: Patient One

FIG. 3A illustrates the timing of iododeoxyuridine infusion courses administered to the first historic HAT-Pi patient (aka Patient One; A.C., a 65-year old woman with metastatic melanoma) who was treated in 1959 in the study cited in Table 1a. This illustration, adapted from Chart#3 in the original published article, provides a longitudinal record of the timing of her subjective and objective responses, and her hematology record showing the timing of myelosuppression nadirs over a 5-month course of treatment.

Historic HAT-Pi Patient One; Pain Relief and Reversibility

Compelling evidence for a causal relationship between extended HAT treatment and symptom improvement is evident from a day-by-day longitudinal record of symptom-relief from severe pain (3.0 on a 4.0 scale) to manageable pain (0.5 on a 4.0 scale). FIG. 3A illustrates how the timing of her HAT infusion courses compared with the timing of her subjective and objective responses.

Two Distinct Pain Relief Periods for Historic HAT-Pi Patient One

The first period of pain-relief (PR #1, FIG. 3A) was dramatic because it occurred as a sharp decrease from 3.0 to 0.5, (on a 0-4 scale). The onset also closely followed the first nadir in white blood cell counts (nadir #1, FIG. 3A). Both events followed a 3-week course of multiple intravenous bolus infusions of high concentrations of HAT.

Pain-relief was reversible because it returned, albeit at a reduced level (2.0), after 4-weeks without HAT-Pi. A second course of iododeoxyuridine infusion, which was permissible because white blood cell counts had returned to normal ("normal" was set at 5,000 white blood cells per microliter), was followed by a second period of pain relief (PR #2, FIG. 3A) coinciding also with a second myelosuppression nadir and recovery. A third course of treatment was not attempted for this patient due to an unfortunate and unexpected lack of iododeoxyuridine availability. So, when pain returned, continued HAT-Pi treatment was not possible for this patient.

7. Myelosuppression and Symptom Relief may Coincide During HAT-Pi Treatment

The longitudinal record for Patient One in FIG. 3A illustrates the coincident timing of her myelosuppression nadirs with onset of symptom relief, which is consistent with both resulting from a common underlying cause, namely HAT-Pi. Because these changes are reversible, repeated HAT-Pi treatment courses were necessary to maintain symptom relief, accompanied by intervening periods of HAT-withdrawal, which were necessary to manage myelosuppression.

Underlying reasons for coincidence and reversibility include but are not limited to:

Coincidence

Pain-relief results from cumulative antineoplastic effects resulting from inhibition of PARP1 enzymatic activity, including but not limited to the arrest of tumor cell replication and migration as well as disintegration of arrested tumor cells, both of which may lead to decreased impingement on neighboring tissues which may alleviate pain. The myelosuppression nadir results principally from the anti-differentiation effects of HAT that are well-documented. The coincident timing of both pain relief and myelosuppression illustrated in FIG. 3A are, therefore, signs of HAT-Pi treatment efficacy that are fully consistent with the HAT-Pi molecular and cellular effects outlined here. These coincident signs contribute to milestones for monitoring and assessing any HAT-Pi administration regimen.

Reversibility

Reversibility is an intrinsic characteristic of HAT-Pi treatment because reversibility is an inherent characteristic of competitive enzyme inhibition. For the patient, this translates into reversibility of symptom/pain relief, myelosuppression and tumor regression as well as side effects such as alopecia. Reversibility after withdrawal from HAT-Pi may result of many biochemical and cellular forces including, but not limited to: (a) reduction in the intracellular concentration of HAT; (b) increase in the intracellular concentration of $NAD^+$; (c) increase in the intracellular concentration of ATP; (d) intracellular synthesis of new PARP1 enzyme molecules that have never been exposed to HAT; and, (e) dynamic regeneration of tissue stem cells through intrinsic renewal processes. The latter explanation may account for the relatively rapid kinetics of myelosuppression recovery for Patient One as well as that reported for multiple historic HAT-Pi patients in NIH-sponsored trials.

Figure 3B:
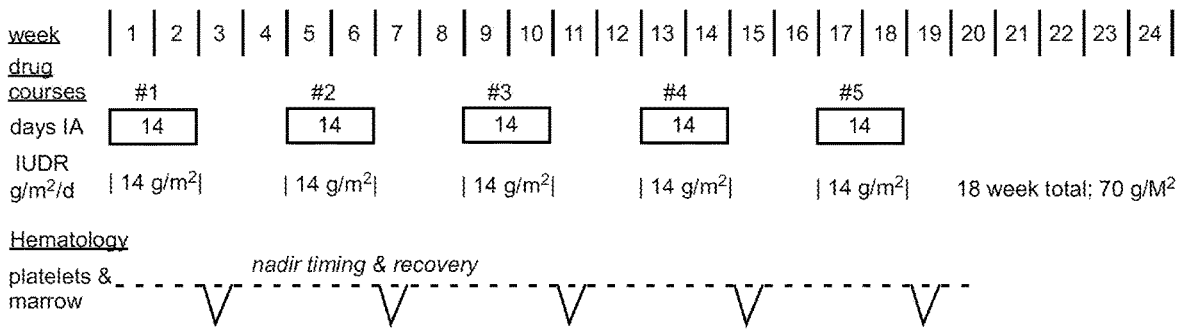

FIG. 3B: NIH Historic HAT-Pi Regimen: Unresectable Sarcoma and Colorectal Liver Metastases FIG. 3B illustrates the 2-week-on/2-week-off timing of iododeoxyuridine courses administered to multiple historic HAT-Pi patients in NIH studies cited in Table 1-d and -f. The reported timing of myelosuppression nadirs and recovery are also shown. Longitudinal records for subjective and/or objective responses were not reported.

Managing Myelosuppression

Myelosuppression must be carefully monitored and managed to ensure the patient safety during the long period of HAT-Pi therapy. NIH studies have outlined effective methods to manage myelosuppression during extended courses of HAT infusion as illustrated in FIG. 3B. In the instances shown, 14 grams of HAT per square meter of body surface was administered by continuous intravenous or intra-arterial infusion over a period of 14 days, followed by a 14 day period of no HAT infusion. The timing of patient myelosuppression nadirs, and recovery, typically occurred within 7-10 days after withdrawal of HAT infusion. In other words, patient blood cell counts generally returned to normal during the scheduled 2-week periods of HAT withdrawal allowing repeated treatment courses over 18 weeks that resulted in objective and subjective improvement, as shown in Table 1-d, -e and -f.

8. Reversibility is a Fundamental Aspect of HAT-Pi Treatment

Reversibility of objective improvement due to the return of neoplastic tumor cell uncontrolled replication and metastases may recur after withdrawal of HAT-Pi treatment. The longitudinal record of Patient One clearly illustrates that subjective and objective improvements are reversible after HAT is withdrawn (FIG. 3A) allowing metastases and tumor mass expansion to once again cause pain to increase. Although only end-point information is available from the NIH studies, a higher proportion of patients experienced stable subjective and objective improvement when HAT-Pi was repeatedly administered over extended periods of multiple weeks and months. Therefore, subjective improvement, and clinically-verified, objective improvements in patient status are correlated with multiple HAT-Pi treatment courses administered over extended periods. Administration of repeated HAT-Pi courses may also overcome the reversibility of symptom improvement. HAT-Pi implementation requires careful management to maintain or increase objective improvements with potentially deleterious side-effects including but not limited to myelosuppression.

HAT-Pi; Potential for Durable Improvements

Neoplastic cell disintegration and death are irreversible results of HAT-Pi treatment on neoplastic cells grown in culture for extended periods, as noted above. The notion that neoplastic cell disintegration and death also occurs in HAT-Pi patients is consistent with reports of tumor size reduction and with subjective improvement (Table 1 and FIG. 3A). Therefore, irreversible disintegration and death of a proportion of neoplastic cells may have contributed to objective improvement in those studies. It remains to be determined if HAT-Pi may eventually lead to permanent elimination of neoplastic tumor cells or long-term reduction in their numbers sufficient to provide enduring relief from the effects of neoplastic disease.

E. HAT Pharmacology and Toxicity in Historic HAT-Pi Patients

HAT Pharmacology

HAT pharmacology in human subjects has been extensively analyzed for the intended purpose of maximizing incorporation of HAT into patient neoplastic tumor cell DNA during clinical studies conducted by and/or with the cooperation of United States National Institutes of Health; (see, for non-limiting examples, Kinsella, 1987 op cit; Chang, 1989 op cit; R. J. Morgan, Jr., E. M. Newman, J. H. Doroshow, K. McGonigle, K. Margolin, J. Raschko, W. Chow, G. Somlo, L. Leong, M. Tetef, S. Shibata, V. Hamasaki, M. Carroll, S. Vasilev, S. Akman, P. Coluzzi, L. Wagman, J. Longmate, B. Paz, Y. Yen, R. Klevecz, Cancer Research 58 2793 (1998); C. A. Schulz, M. P. Mehta, B. Badie, C. J. McGinn, H. I. Robins, L. Hayes, R. Chappell, J. Volkman, K. Binger, R. Arzoomanian, K. Simon, D. Alberti, C. Feierabend, K. D. Tutsch, K. A. Kunugi, G. Wilding, T. J. Kinsella, International Journal of Radiation Oncology, Biology and Physics 59 1107 (2004); R. W. Klecker, Jr., J. F. Jenkins, T. J. Kinsella, R. L. Fine, J. M. Strong, J. M. Collins, Clinical Pharmacology and Therapeutics 38 45 (1985); T. J. Kinsella, J. Collins, J. Rowland, R. Klecker, Jr., D. Wright, D. Katz, S. M. Steinberg, E. Glatstein, Journal of Clinical Oncology 6 871 (1988); and references therein). The analytical calibration of HAT dosing by pharmacology analysis was directed toward attaining the highest tolerable HAT concentration levels in patient plasma and maintaining those levels over extended periods. The dual goals were to calibrate HAT dosages that would maximize incorporation of HAT into the DNA of replicating neoplastic tumor cells but that would also minimize side-effects to be generally tolerable and, most importantly, to allow myelosuppression to be comprehensively managed in patients with advanced neoplastic disease.

Patients in the earliest HAT clinical trials, such as the one shown in FIG. 3A, received a concentrated solution of HAT as a daily bolus infusion. Plasma concentrations of HAT may have transiently exceeded 10 micromolar but, due to rapid HAT clearance, plasma HAT concentrations continuously diminished over the next 24 hours. Later trials sought to expose individual patients to a constant plasma concentration of HAT through continuous infusion of HAT (24/7) over 14-day-long or 28-day-long periods. By those methods, constant HAT plasma concentrations could be maintained near, at, or above a concentration level of at least one micromolar HAT for an indefinite period. Using continuous circulatory HAT infusion (iododeoxyuridine) steady-state HAT plasma concentrations in excess of 1.0 (one) micromolar and higher were achieved and tolerated by most patients.

Pharmacological analyses have also demonstrated that catalytic cleavage of bromodeoxyuridine and/or iododeoxyuridine results in accumulation of break-down products, bromouracil and/or iodouracil to concentration levels as much as 100 times higher in patient plasma than the respective parent drug. Bromouracil and iodouracil have demonstrated capacity to inhibit PARP1 enzymatic activity. Their presence in plasma at the elevated concentration ranges observed may substantially contribute to both the extent and duration of PARP1 enzyme activity inhibition and the antineoplastic effects resulting from HAT-Pi administration.

HAT Toxicity

The temporal relationship between HAT-Pi and resulting patient toxicities, which are partially illustrated in FIG. 3A, have been extensively documented in multiple published clinical studies including those cited in Table 1. Myelosuppression is the most serious major side-effect resulting from HAT-Pi and most historic HAT-Pi patients were reported to have experienced neutropenia and thrombocytopenia.

Because myelosuppression may become life-threatening, patient blood status was monitored frequently in those studies to avoid potentially dangerous nadirs in blood cell counts. Blood cell count nadirs were used as the primary determinants of the timing of HAT-Pi treatment withdrawal in the first HAT-Pi regimen (FIG. 3A). Because that study employed 2-hour bolus infusions, patients were transiently exposed to very high concentrations of HAT that may have caused precipitous changes in blood cell status. However, later studies, employing regimens consisting of an alternating schedule comprised of 2-week periods of continuous (24/7) HAT-infusion followed by 2-weeks of no-HAT-infusion (FIG. 3B), showed that patient blood cell counts generally returned to normal within 7-10 days after HAT-withdrawal and well prior to the next scheduled 2-week HAT infusion period. Therefore, management of myelosuppression is feasible in most patients through careful control of HAT plasma concentrations and close monitoring of patient blood cell counts.

Alopecia leading to total baldness is a common side effect reported for historic HAT-Pi patients. Other common side effects include, but are not limited to; nausea/vomiting, mucositus/stomatitis, diarrhea, and skin rash, which were reported for a minority of patients. In some patients one or more of these non-life-threatening side-effects were severe to the point that HAT-Pi treatments were withdrawn due to side-effect intolerance.

F. HAT-DNA Cannot Explain HAT Anti-Neoplastic Effects

HAT-DNA concepts for treatment of neoplastic disease generally include but are not limited to:

1. Fragile HAT-DNA

Hypotheses that radiation treatment is more efficient at killing neoplastic cells possessing HAT-DNA are not pertinent because radiation is not relevant to the HAT-Pi concept or mechanism.

2. Fraudulent. HAT-DNA

Published statements asserting that HAT-DNA exerts anti-neoplastic effects through inaccurate or incorrect coding of genetic information, or other DNA-based mechanism have not been substantiated. While HAT-DNA is synthesized in HAT-exposed neoplastic cells, the presence of HAT-DNA in those cells cannot exert the anti-neoplastic effects attributable to HAT, either in cultured neoplastic cells or in patients with advanced neoplastic disease. The reasoning behind that assertion is based on consideration of issues including but not limited to the following:

a. Reversibility Inconsistent with Stable Incorporation into DNA

HAT anti-neoplastic effects observed in patients are reversible despite the fact that HAT-DNA remains present. Anti-neoplastic effects in culture (outlined in C, above) appear within 24 hours after HAT-exposure and are maintained as long as HAT is in the culture medium. If HAT is withdrawn within the first few days then the characteristic neoplastic cell behaviors (uncontrolled cell replication, absence of contact inhibition, and substrate-attachment-independence) gradually return despite the continued presence of HAT-DNA. Therefore, early reversibility is not consistent with a HAT-DNA-based mechanism.

b. Quantitative Relationship to DNA Incorporation Lacking

Anti-neoplastic cell effects are fully evident within 24 hours after neoplastic cells in culture are exposed to low micromolar HAT concentration levels. Considering that time period, and the low concentration of HAT, relatively low levels of HAT have been incorporated into DNA. In addition, cultured neoplastic cells become arrested within 24 hours after HAT-exposure, at a time when only a fraction ($\sim 1/4$-$1/2$) of neoplastic cells have completed DNA replication and incorporated HAT into their DNA. Therefore, the remaining fraction of neoplastic cells ($\sim 1/2$-$3/4$) have not yet incorporated any HAT into their DNA but the abnormal neoplastic cell behavior and morphology of these cells is also altered in the same way by the presence of HAT. Quantitative increases in HAT incorporation into DNA, achieved by increasing HAT concentration in the culture medium, lead neither to quantitative nor qualitative differences in anti-neoplastic effect.

Similarly, in patients exposed to HAT, a minority of neoplastic cells actually incorporate HAT into their DNA molecules. Repeated administration of HAT leads to anti-neoplastic effects that cannot be attributed to substantially higher levels of HAT-DNA.

The HAT-DNA mechanism has no explanation for how the HAT anti-neoplastic effects are imposed on neoplastic cells that do not have HAT in their DNA. The objective and subjective responses of patients to repeated HAT exposure cannot be reconciled with the low HAT-DNA incorporation levels observed.

c. No Consensus or Accepted Hypothesis Explains HAT Anti-Neoplastic Effects.

No generally accepted hypothesis has been proposed to explain how a common set of anti-neoplastic changes occur globally within a population of cultured neoplastic cells, some of which have incorporated HAT into varying segments of their chromosomal DNA and some which have not incorporated any HAT into their DNA, nor how such changes occur in common amongst virtually all cultured neoplastic cell types upon HAT-exposure.

H. HAT Anti-Neoplastic Effects are Fully Consistent with an Enzyme Inhibition Mechanism Enzyme inhibition by HAT is mechanistically consistent with each of the properties outlined above that are inconsistent with the HAT-DNA model.

1. Reversibility is an Intrinsic Aspect of Enzyme Inhibition

Reversible inhibition is a fundamental characteristic of enzyme regulation, including product inhibition and inhibition by allosteric regulators which inhibit enzyme activity by reversibly binding to an enzyme in a concentration-dependent manner. Reversibility of HAT anti-neoplastic effects is attributable to reversible inhibition of PARP1 enzymatic activity. The parallel formation of HAT-DNA is mechanistically unrelated to these anti-neoplastic effects.

2. Quantitative Threshold of HAT Concentration and Inhibition of PARP1 Enzymatic Activity Enzyme inhibition is dependent upon inhibitor concentration. In the case of HAT, concentrations in the low micromolar range are sufficient to inhibit PARP1 enzymatic activity. More elevated HAT concentrations cannot have an added effect. Accordingly, the dis-inhibition of PARP1 enzymatic activity, after HAT withdrawal, is also concentration dependent as inhibitor concentrations become progressively reduced. The observable rate of dis-inhibition may also be affected by other factors including but not limited to: a) concentration-dependent competition by the natural substrate, $NAD^+$; b) the potential presence of other inhibitors, natural or pharmaceutical; and c) synthesis of new PARP1 enzyme molecules.

3. HAT Emulates and Amplifies Thymidine Regulatory Roles

Structural Similarity between Thymidine and HAT Molecules

Figure 4A:
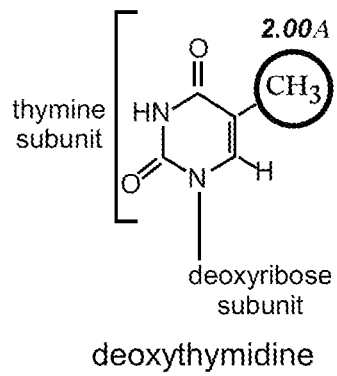
FIGS. 4 A-D provide diagrams illustrating HAT drug chemical structures.
Figure 4B:
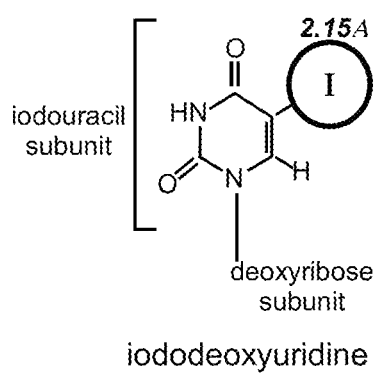
Figure 4C:
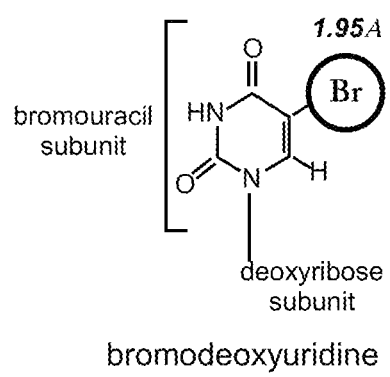

The molecular structure of the natural metabolite thymidine (aka deoxythymidine; FIG. 4A) is mimicked by the molecular structures of the HAT molecules iododeoxyuridine (FIG. 4B) and bromodeoxyuridine (FIG. 4C). Each contains an identical deoxyribose subunit attached to base subunits, thymine, iodouracil and bromouracil, respectively, which differ only in the atomic composition at their 5' (five-prime) positions. The thymine subunit has a methyl group ($CH_3$ in FIG. 4A representing a single carbon atom with 3 hydrogen atoms attached). In HAT molecules the methyl group is replaced by a single halogen atom, either iodine or bromine (FIGS. 4B and 4C). The diameters of these two halogen atoms (iodine, 2.15 Ångstrom units; bromine 1.95 Ångstrom units) closely approximate that of the methyl group on the thymine subunit of thymidine (2.00 Ångstrom units) a fact that is generally accepted to account for the ability of HAT molecules to be "recognized and utilized" as thymidine molecules within cells. The higher electron density of the halogen atoms in HAT molecules, in comparison to the methyl group in thymidine molecules, is one potential non-limiting explanation for the ability of HAT molecules to inhibit PARP1 enzymatic activity at concentrations much lower than the natural inhibitors, thymidine and thymine (Preiss, 1971 op cit; Pivazyan, 1992 op cit).

Thymidine Abundant in Replicating Cells

The major structural role of thymidine in biological systems is as a nucleotide in DNA polymers where it comprises the letter "T" in the 4-letter (GATC) genetic code alphabet. Thymidine, as a "free" molecule, is abundant only in cells actively synthesizing DNA where new thymidine-monophosphate molecules are synthesized de novo by methylation of deoxyuridine monophosphate, through the combined interaction of two enzymes; thymidylate synthase and dihydrofolate reductase. In cells actively engaged in DNA synthesis (cells that are in S-Phase of the cell cycle), the phosphorylated forms of thymidine and corresponding phosphorylated forms of HAT, potentially: a) incorporate into newly-synthesized DNA; and, b) act as allosteric regulators of enzymes in the DNA synthetic pathway. While the later was initially judged to be insufficient to account for the cell-cycle-arrest effects of HAT treatment (Y. S. Bakhle and W. H. Prusoff, Biochimica et Biophysica Acta 174 302 (1968) and references therein) the discovery of the existence of thymidine-regulated cell cycle progression indicates that allosteric regulation by thymidine may be an important regulator of cell cycle progression in actively replicating blood precursor cells (W. R. Austin, A. L. Armijo, D. O. Campbell, A. S. Singh, T. Hsieh, D. Nathanson, H. R. Herschman, M. E. Phelps, O. N. Witte, J. Czernin, C. G. Radu, Journal of Experimental Medicine 209 2215 (2012) and references therein). This link to the natural regulatory thymidine may provide an inroad toward improving the understanding and management of myelosuppression in HAT-Pi patients.

Thymidine Molecules are Rare in Non-Replicating Cells (G1/0 Cells)

Non-replicating cells (cells in the G-1 and/or G-0-phase of the cell cycle) comprise the vast majority of cells in most tissues and organs of the body and may also be the cell cycle stage that predominates in many tumors. In such non-replicating cells, the DNA synthetic enzyme pathways are inactive including those required for the synthesis of new thymidine molecules. In non-replicating cells, the only potentially abundant source of free thymidine (i.e. thymidine that is not part of a DNA molecule) is from outside the cell membrane; in other words, from the blood plasma, tissue space or cell culture medium.

Thymidine: Anti-Neoplastic Effects

Figure 2A:
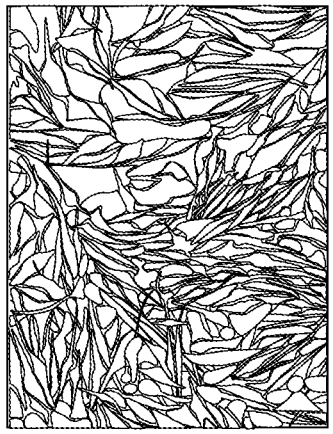
FIGS. 2 A-D illustrate HAT-Pi effects on human neoplastic cells in culture.
Figure 2B:
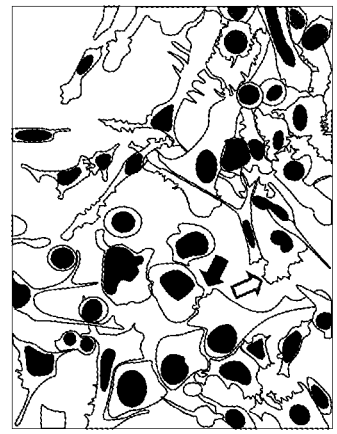
Figure 2C:
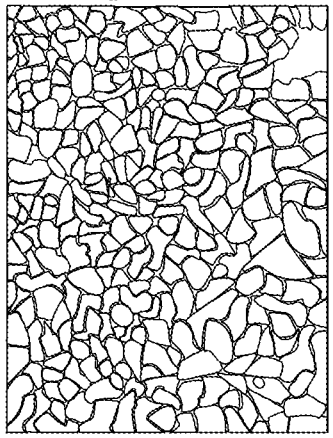
Figure 2D:
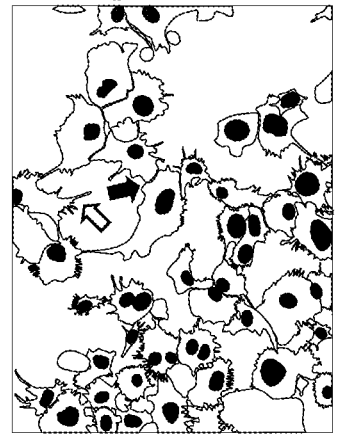

Thymidine, when present at concentrations in excess of 1.0 (one) millimolar in cell culture, induces HeLa cells (a human neoplastic cell line) to attach, flatten and undergo cell death and disintegration (E. Sumikawa, Y. Matsumoto, R. Sakemura, M. Fujii, D. Ayusawa, Biochemical and Biophysical Research Communications 335 558 (2005) and references therein), anti-neoplastic effects comparable to those induced by 10.0 (ten) micromolar HAT (FIGS. 2B and 2C). The explanation for the 100-fold lower concentration required for HAT to elicit anti-neoplastic effects includes but is not limited to: a) lower PARP1 inhibitory strength of thymidine as compared to HAT; and, b) cellular regulatory mechanisms that control cellular uptake of excessive levels of thymidine but which may be unable to similarly control excessive levels of HAT uptake.

4. Thymidine and HAT as PARP1 Inhibitors; Roles Outside DNA Metabolism

Thymidine is capable of inhibiting at least one enzyme not involved in metabolism of nucleosides and DNA, namely, Poly (ADP-ribose) Polymerase 1 (PARP1). PARP1 protein is present in both replicating and non-replicating cells, where its enzymatic activity is susceptible to inhibition by thymidine and HAT.

Replicating Cells

In replicating S-phase cells, or non-S-phase cells undergoing DNA repair, thymidine molecules present at sites of DNA synthesis in chromatin may inhibit PARP1 activity at these sites. HAT molecules are actively imported into S-phase cells which potentially increases its ability to inhibit PARP1 in such cells.

Non-Replicating Cells

In non-replicating cells, by contrast, inhibition of PARP1 enzymatic activity by thymidine is reduced because, as noted above, molecules of free thymidine and/or thymine are generally rare or absent inside non-replicating cells. However, in the presence of extracellular HAT (in the plasma or culture medium) at low micromolar concentrations, nucleoside facilitative transport allows entry of HAT inside all exposed cells, both replicating and non-replicating, to a concentration that may approach or match the extracellular concentration.

Extracellular HAT in the low micromolar concentration range has the potential to inhibit PARP1 enzymatic activity in all exposed cells. In neoplastic cells, specifically, intracellular equilibration of exogenous HAT in low micromolar concentration may be expected to inhibit PARP1 enzymatic activity of all types, including, but not limited to PARP1 auto-modification and trans-modification of PARP1 target proteins.

I. Summary and Conclusion: HAT Anti-Neoplastic Effects Result from HAT-Pi

In conclusion, HAT antineoplastic effects are fully consistent with a enzyme inhibition mechanism. PARP1 is an enzyme that is inhibited by HAT within the low micromolar concentration range, which is similar to the low micromolar HAT concentrations that induce anti-neoplastic effects in neoplastic cell culture. Human patients with advanced neoplastic disease have experienced objective and subjective improvement after extended exposure to plasma concentrations of HAT in excess of 1.0 micromolar.

HAT-Pi Hypothesis for Treatment of Neoplastic Disease

The HAT-Pi hypothesis asserts that HAT exerts anti-neoplastic effects by competitive inhibition of PARP1 enzyme activity in neoplastic cells. That hypothesis is supported by multiple lines of evidence, discussed above and including, but not limited to, the following summary statements:

1. HAT Inhibits Enzymatic Activity of Purified PARP1

In vitro experiments using purified PARP1 show that its enzymatic activity is competitively inhibited by HAT at concentrations in the low micromolar range, comparable to prototypic PARP1 inhibitors. As an analog metabolite, HAT uptake by cells cultured in the presence of low micromolar HAT results in HAT concentration inside neoplastic cells approaching, equaling or exceeding the extracellular concentration. In other words, low micromolar HAT concentrations are sufficient to inhibit enzymatic activity of purified PARP1 in solution and low micromolar HAT concentrations in medium are sufficient to inhibit intracellular PARP1 enzymatic activity of cultured neoplastic cells.

2. HAT Inhibits Abnormal Neoplastic Cell Behaviors in Cell Culture

HAT at low micromolar concentrations restores substrate-adhesion-dependent survival, cell-cell communication and cell-contact-inhibited replication and movement in cultured neoplastic cells in a fashion similar to known PARP1 inhibitors and by thymidine.

3. HAT in Patient Plasma for Extended Periods Exerts Anti-Neoplastic Effects

Clinical studies of patients with advanced neoplastic disease, that included HAT infusions that achieved patient plasma HAT concentrations in excess of one (1.0) micromolar for extended periods, resulted in decreased symptoms and tumor shrinkage in patients with advanced neoplastic disease.

4. Concentration-Dependence and Reversibility are Characteristics Compatible with Enzyme-Inhibition The characteristic concentration-dependence and reversibility of HAT anti-neoplastic effects are fully consistent with an enzyme inhibition mechanism while inconsistent with a DNA-based mechanism.

5. Conclusion

The effects of HAT on neoplastic cells is the result of inhibition of the enzymatic activity of PARP1 and that HAT-Pi has potential as a treatment for patients with advanced neoplastic disease.

II. HAT-Pi Chemotherapy: Concepts and Strategies

The previous section concerned the unexpected discoveries made using existing published and unpublished information that lead to invention of the HAT-Pi treatment method. The historic HAT-Pi patients were generally infused with HAT in quantities intended to maximize incorporation of HAT into neoplastic tumor cell DNA. These studies established the maximum tolerated dosage of HAT as well as methods required to monitor and manage side effects. Importantly, the HAT plasma concentrations attained in those studies were in excess of 1.0 micromolar, a concentration sufficient to partially or completely inhibit intracellular PARP1. Therefore, already-proven infusion methods are directly applicable to the same goal in HAT-Pi strategy; to maximize concentrations of HAT in plasma of patients with advanced neoplastic disease to inhibit PARP1 enzymatic activity in neoplastic tumor cells.

The current section outlines and defines unique characteristics of HAT-Pi treatments including, but not limited to, its antineoplastic effects in patients, and possible molecular targets that may be affected through inhibition of PARP1 enzymatic activity.

HAT-Pi; A New and Palliative Treatment for Advanced Neoplastic Disease

1. Distinguishing and Unique Characteristics of HAT-Pi Chemotherapy

The overall strategy of HAT-Pi treatment for neoplastic disease is new and unexpected in several respects. First, it is a new chemotherapy strategy to use HAT as an enzyme inhibitor, rather than as a DNA precursor. Second, inhibition of PARP1 enzymatic activity is the primary treatment modality, whereas prior clinical use of PARP1 inhibitors has been as chemotherapeutic adjuvants, or secondary agents, to inhibit repair of DNA damaged by either ionizing radiation or chemotherapy as the primary treatment modality. Third, HAT-Pi chemotherapy is cytostatic for neoplastic cells with minimal and manageable side effects on normal tissues and organs as compared to conventional cell-kill (cytolytic) chemotherapy which typically exerts deleterious effects on the functioning of normal tissues and organs. Fourth, HAT-Pi treatment has the potential to reduce neoplastic disease-associated pain and thereby reduce the need for 3rd stage analgesic medications such as opioids and opioid-related drugs that are currently the primary method for treating such uncontrolled pain. Fifth, neoplastic cell suicide may result in partial or complete tumor regression after chronic HAT-Pi exposure over extended periods. Finally, HAT-Pi chemotherapy may be useful for treatment of a range of conditions that may involve dis-regulation of PARP1 enzymatic activity.

2. HAT-Pi For an Unaddressed Treatment Interval in Symptom Management

The HAT-Pi treatment methods described here may be employed to address a specific interval in the current prevailing strategy for treatment of pain in patients with advanced neoplastic disease. That interval is best defined as a period that is: (a) after the decision to cease or forego other conventional anti-tumor treatment methods; and, (b) prior to the onset of patient-usage of opioid/opioid-related medication as the primary or exclusive mode of disease-related pain-relief. A central objective of HAT-Pi treatment for such patients is to provide an alternative method of pain relief and to postpone, for an extended but indefinite period, the need for opioid/opioid-related medication.

HAT Chemical Identities

1. HAT Drugs are Analogs of Thymidine.

HAT drugs and compounds are so-named because of their structural similarity to thymidine (FIG. 4A). The term "HAT" is an acronym for Halogenated Analog of Thymidine and specifically refers to uridine compounds with an atom of either bromine or iodine in the 5' position where thymidine has a methyl group (comprising 3 hydrogen atoms bonded to an atom of carbon). HAT drugs for administration to patients includes one or a combination of:

Iododeoxyuridine (FIG. 4B)
   aka: 5-iododeoxyuridine; IUDR (multiple acronyms exist); NSC#39661; PubChem CID: 5905

Bromodeoxyuridine (FIG. 4C)
   aka: 5-bromodeoxyuridine; BUDR (multiple acronyms exist); NSC#38297; PubChem CID: 6035

IPdR; a HAT prodrug (FIG. 4D)
   aka: 5-iodo-2-pyrimidinone-2'-deoxyribose; IPdR; NSC#726188; PubChem CID: 14326905

2. HAT Drugs Include Related Precursors and Metabolic Products that Inhibit PARP1 Activity.

HAT drugs are metabolized in human patients. Catabolic products that accumulate in plasma to concentration levels that are consistent with inhibition of PARP1 enzyme activity in neoplastic cells include, but are not limited to:

a) Iodouracil; a Halogenated Analog of Thymine

Iodouracil is expected to accumulate in plasma of HAT-Pi patients due to catabolic degradation of iododeoxyuridine by liver enzymes including, but not limited to, dihydrouracil dehydrogenase. Both iodouracil and bromouracil are predicted to have PARP-1 inhibitory capacity at concentrations observed in patient plasma and may have contributed to partial or complete inhibition of PARP1 enzymatic activity in neoplastic tumor cells that lead to anti-neoplastic effects observed in historic HAT-Pi patients. Therefore, products of HAT catabolism, including but not limited to bromouracil and iodouracil, are to be considered HAT drugs to any degree of inhibition of PARP1 enzymatic activity and regardless of source.

b) Other Halogenated Nucleoside Potential Precursors to HAT

Halogenated cytosine nucleosides, as one non-limiting example, may serve as metabolic precursors leading to formation of 5-bromouracil, 5-bromodeoxyuridine, 5-iodouracil, and/or 5-iododeoxyuridine within neoplastic cells. A HAT drug, as used in this invention, includes any such compound that leads to production of HAT molecules for the purpose of inhibiting PARP1 enzymatic activity.

3. The Term "HAT" as Employed here, is not Related to any other Usage of this Acronym.

The acronym "HAT" employed here uniquely represents halogenated analogs of thymidine as defined above and bears no relationship to any other use of the "HAT" acronym for any use or purpose, including but not limited to:

Hypoxanthine-Aminopterin-Thymidine (HAT) Selection Medium

An unrelated use of the acronym "HAT" describes a medium which contains hypoxanthine, aminopterin and thymidine that is used for cell-selection in culture for creation of, for a non-limiting example, hybridoma cell clones (G. Kohler and C. Milstein, Nature 256 495 (1975) and references thereto) or any other purpose.

Any HAT Acronym Referring to a Matter or Subject Unrelated to Halogenated Analogs of Thymidine The acronym "HAT" employed here has no relationship to any HAT term or acronym that is presently known or unknown.

HAT-Pi Treatment: Conceptual Overview

1. HAT-Pi Treatment for Advanced Neoplastic Disease: Methods and Goals

HAT-Pi Treatment Method

HAT-Pi treatment involves administration of one or more HAT drugs to a patient with neoplastic disease in a manner that results in partial or complete inhibition of PARP1 enzymatic activity in neoplastic tumor cells over extended periods.

HAT-Pi Treatment Goals a) Inhibition of PARP1 enzymatic activity results in the arrest of neoplastic tumor cell uncontrolled replication and uncontrolled metastatic movements of neoplastic tumor cells.

b) Chronic PARP1 inhibition may result in progressive disintegration and death of neoplastic tumor cells thereby reducing the size of some or all tumor masses.

c) The combined effects of a and b may reduce pain associated with advanced neoplastic disease.

d) The combined effects of a, b, and c may extend life and improve feelings of well-being in patients with advanced neoplastic disease.

2. HAT-Pi Treatment for Advanced Neoplastic Disease: Concentration- and Time-Dependent Variables Background PARP1 enzymatic activity in vitro is inhibited by HAT in the low micromolar concentration range (FIG. 1). One gram of HAT (iododeoxyuridine) per square meter patient skin per day by continuous infusion maintains plasma and tissue space concentrations of HAT at or above the one micromolar concentration range. HAT circulating at that concentration may partially or completely inhibit intracellular PARP1 enzymatic activity in all tissues, and all neoplastic cells in particular, either singly or in tumor masses, by virtue of the ability of HAT to enter cells by facilitative transport thereby, essentially, equalizing intracellular and extracellular HAT concentrations. Objective improvements and subjective symptom relief have been reported for patients that received HAT at these dose levels over extended time periods (see Table 1, FIG. 3 and related text).

HAT Plasma Concentration and Duration of Exposure

The information from historic HAT-Pi patients indicates that PARP1 inhibition and anti-neoplastic effects result when HAT is administered at a rate that yields HAT concentrations in excess of 1.0 micromolar in patient plasma. Some historic HAT-Pi patients tolerated sustained HAT plasma concentrations in excess of 5 micromolar and even higher concentrations that may have gone unmeasured and/or undocumented.

Therefore, for an initial course of administration of HAT-Pi treatment, the target HAT plasma concentration is at least 1.0 (one) micromolar, with that concentration sustained over an extended period, consisting of between one week and four weeks, and followed by one to two weeks without HAT administration.

HAT-Pi Catabolites: Concentration and Persistence in Patient Plasma

Catabolism of infused HAT (either bromodeoxyuridine or iododeoxyuridine) leads to formation of breakdown products, bromouracil and iodouracil, which may accumulate in patient plasma to concentrations that approach 100 micromolar, and which may also contribute significantly to inhibition of intracellular PARP1 enzymatic activity and are, therefore, also defined as HAT drugs for the purposes of this invention. Iodouracil and bromouracil may persist in patient bloodstream longer than the parent molecules and at higher concentrations that may contribute to the sustained inhibition of PARP1 enzymatic activity in neoplastic tumor cells for an indeterminate period after withdrawal of HAT administration.

HAT-Pi Maintenance: Maximum and Minimum Concentration Targets

In historic HAT-Pi patients, once inhibition of PARP1 enzymatic activity was achieved it was maintained by repeated infusion of HAT into patient plasma at the same or higher concentration level as was employed in the initial infusion.

It is reasonable to anticipate, however, that after an initial course of HAT-Pi, it may be possible to maintain PARP1 inhibition using modified HAT-Pi infusion protocols including, but not limited to:

a) using lower HAT plasma concentration target(s) that are below 1.0 micromolar;
b) using alternative HAT types;
c) combining HAT with use of a non-HAT-type of PARP1 inhibitor;
d) combining HAT with any alternative method of inhibiting PARP1 enzymatic activity; or
e) any combination of the above.

Summary: HAT-Pi Concentration Range

HAT-Pi anti-neoplastic effects may result over a broad range of HAT plasma concentrations that depend upon many factors including, but not limited to, the formation of HAT metabolites due to patient metabolism and the need to minimize side-effects while maintaining PARP1 inhibition over extended periods. Such considerations lead to definition of a broad operational concentration range for HAT-Pi as: Exposure of neoplastic tumor cells or tissue to one or more HAT drugs, or catabolic product, at plasma or tissue space concentrations between one tenth (0.1) micromolar to one hundred (100) micromolar. That broad range attempts to account for: a) the expectation that maintenance of HAT-Pi may require lower HAT concentrations than the first-exposure inhibition of PARP1 enzyme molecules by HAT; b) the relatively higher plasma concentration of HAT metabolites which are expected to contribute to inhibition of PARP1 enzymatic activity in neoplastic tumor cells; c) the potential for combinatorial use of HAT drugs and with PARP1 inhibitors of differing chemical identity; and, d) the multiple potential routes of HAT administration.

HAT-Pi: Cytostatic Effects

Neoplastic cells cultured in the presence of HAT in the low micromolar range (between 1.0 and 20.0 micromolar) rapidly undergo cytostatic changes which typically appear within the first 24 hours of HAT exposure and are sustained as long as HAT-Pi exposure is maintained. The early cytostatic effects include, but are not limited to:

1. Arrest of Uncontrolled Neoplastic Cell Replication by Cell-Intrinsic Mechanisms Neoplastic cells in G1 phase at the time of HAT exposure become "G1-arrested" and remain so during HAT-Pi exposure. Neoplastic cells that are actively synthesizing DNA (S phase) may complete S phase but become subsequently arrested in the G1 or G2 phase of the cell cycle during HAT-Pi exposure.

2. Arrest of Uncontrolled Neoplastic Cell Replication by Restoration of Contact Inhibition Uncontrolled replication of HAT-Pi treated neoplastic cells becomes inhibited through formation of cell-cell boundaries (contact inhibition).

3. Arrest of Uncontrolled Motility of Neoplastic Cells by Substrate Attachment and Contact Inhibition HAT-Pi treated neoplastic cells become flattened and strongly attached to substrate restricting cell motility. Cell movement and migration is further restricted by contact inhibition that is triggered by cell-cell contact and formation of cell-cell boundaries.

HAT-Pi: Cytolytic Effects

HAT-Pi cytolytic effects are progressive and may not affect 100% of exposed neoplastic cells during any specific period and, therefore, permanent (irreversible) tumor regression and/or total eradication of neoplastic tumor cells may not be obtainable with HAT-Pi treatment.

The underlying causes of HAT-Pi cytolytic effects include, but are not limited to:

1. Substrate-Attachment-Dependent Survival

In the presence of HAT-Pi, cultured neoplastic cells that are not substrate-attached do not survive. The fate of unattached neoplastic cells in HAT-Pi patients is unknown. However, based on observations of neoplastic cell culture behavior after exposure to HAT-Pi, as outlined above, a portion of the neoplastic cells in a patient body may be expected to disintegrate and die in a similar manner as observed in neoplastic cell culture;

Some tumor cells may be particularly sensitive to the cytolytic effects of HAT-Pi including the following non-limiting examples: a) metastatic cells may lack substrate-attachment particularly during migration; b) neoplastic cells inside tumor masses may have no access to substrate available for attachment;

2. Neoplastic Cell Disintegration Through Cell-Intrinsic Mechanisms

Neoplastic cell disintegration after HAT-Pi exposure for several weeks may occur through cell-autonomous mechanisms including, but not limited to, cell senescence and apoptosis (Levkoff, 2008 op cit and references therein); and 3. Potential Toxicity from Neoplastic Cell Disintegration Because neoplastic cell death may lead to toxicity from cell break-down products the potential for such toxicity should be considered and distinguished from HAT-Pi side-effects per se.

HAT-Pi: Effects in Patients with Advanced Neoplastic Disease

The anti-neoplastic effects of HAT in neoplastic cell cultures are related to antineoplastic effects observed in patients exposed to HAT-Pi in the manner outlined below.

1. Subjective Improvement

The uncontrolled expansion and metastasis of tumor cells in patients' bodies are generally considered to be related to abnormal behaviors observed for neoplastic cells in culture. Abnormal behaviors of neoplastic cells in culture include but are not limited to:

a) uncontrolled neoplastic tumor cell replication;
b) absence of contact inhibition of neoplastic tumor cell replication, growth and movement; and
c) absence of substrate-attachment-dependence for neoplastic cell survival.

Accordingly, in the body, the uncontrolled replication and lack of contact inhibition of neoplastic tumor cells (i.e. neoplastic cells within tumor masses) contribute to uncontrolled tumor expansion, causing physical impingement upon normal tissues which may cause pain. Metastatic cell migration is dependent upon the ability of neoplastic cells to survive in the absence of substrate attachment which underlies the ability of metastatic cells to colonize, grow and cause pain at other sites in the body.

Given the above framework, patient pain-relief in particular and symptom-relief in general are attributed to specific effects on tumor cells that include, but are not limited to:

a. Pain Relief Owing to Arrest of Uncontrolled Replication of Tumor Cells.

Uncontrolled replication of neoplastic tumor cells leads to tumor growth and expansion that impinges on neighboring tissues. Arrest of uncontrolled neoplastic tumor cell replication stops tumor growth thereby reducing pain from the pressure of tumor impingement on non-tumor tissues.

Although the arrest of uncontrolled neoplastic tumor cell replication may occur within days after initiation of HAT-Pi treatment, the onset of pain relief may not occur until one or more treatment weeks have elapsed. The reasons for such a lag period are not understood.

b. Pain Relief Owing to Tumor Cell Disintegration and Death

Disintegration and elimination of tumor cells may reduce tumor volume thereby reducing pain by decreasing the pressure of tumor impingement on non-tumor tissues. The time-dependent elimination of dead tumor cells could also have toxic consequences which may also contribute to delay the onset of pain-relief.

c. Palliative use of HAT-Pi Treatment

HAT-Pi treatment for advanced neoplastic disease is palliative. Due to the reversible nature of HAT-Pi therapy, the potential exists for residual surviving tumor cells to resume neoplastic behavior and growth patterns. Repeating HAT-Pi treatment regimens may be required for long-term maintenance of tumor-suppression and/or pain-relief.

2. Objective Improvement a. Metastasis Inhibition

Migrating tumor cells that are not substrate-attached (i.e. anchored to a basement membrane structure in a tissue) may disintegrate and/or die after extended HAT-Pi-exposure in a manner similar to that observed for non-adherent neoplastic cells cultured in the presence of HAT. The elimination of dead metastatic tumor cells poses the same issues as outlined above.

b. Tumor Regression

Neoplastic cells in culture disintegrate in substantial numbers after chronic (>14 days) exposure to HAT-Pi and similar disintegration may lead to tumor regression in patients. Measurable tumor regression may require repeated HAT-Pi treatment courses over extended periods that may vary according to many factors, including but not limited to, tumor type, size and location or any property that may affect HAT-Pi exposure and/or elimination of dead tumor cells, as outlined above. Some tumors may not regress for unknown reasons.

3. Reversibility and Potential for Sustained Subjective and Objective Improvement Pharmacokinetic analysis shows that iododeoxyuridine is rapidly eliminated and iododeoxyuridine levels in patient plasma decline to concentrations below the micromolar range, in which case PARP1 enzymatic activity may return for a combination of reasons that include, but are not limited to: (a) dis-inhibition of PARP1 enzymatic activity due to dissociation of HAT molecules from PARP1 molecules as a result of HAT concentrations falling below the low micromolar range; (b) imbalance of physiological regulators; and/or (c) synthesis of new PARP1 enzyme molecules inside neoplastic cells.

Symptom Improvement and Reversibility

Sustained relief from pain and other symptoms is a primary goal of HAT-Pi treatment. Because symptom relief is reversible, repeated HAT-Pi courses may be necessary to maintain symptom relief over extended periods. Symptom relief may occur in the absence of (apparent) commensurate change in objective measures like tumor regression. This is unexplained. Patient-subjective evaluation of symptom improvement, as a primary HAT-Pi goal, may be sufficient reason for continuation of HAT-Pi treatment, even in the absence of measurable sign(s) of objective improvement.

Objective Improvement and Reversibility

Objective improvement in HAT-Pi patients may include, but is not limited to, tumor regression, node regression, reduction in metastases or any objective sign or measure of neoplastic tumor mass decrease or arrest in growth. Objective improvements are also potentially reversible after HAT-Pi due to recovery of arrested neoplastic tumor cells that may survive. Objective tumor responses and reversibility may vary: a) according to tumor types and in different patients; and, b) in tumor masses at different sites in the same patient. This is unexplained. Objective improvement may potentially be sustained through repeated HAT-Pi courses as outlined above for subjective improvement.

Unknown Potential for Permanent Elimination of Viable Neoplastic Tumor Cells An objective "cure" of neoplastic disease, meaning death and or elimination of all neoplastic tumor cells within a patient body and non-recurrence, is not claimed for HAT-Pi treatment for advanced neoplastic disease. No longitudinal study has assessed for the potential of extended HAT-Pi treatment regimens to suppress tumor growth over the long-term, or to eliminate tumor cells completely from a patient's body. Therefore, the potential for HAT-Pi treatment to completely eliminate neoplastic disease remains to be determined.

HAT-Pi: Cellular and Molecular Anti-Neoplastic Effects

Anti-neoplastic effects that result from the inhibition of PARP1 enzymatic activity in neoplastic cells as a result of HAT-Pi may include, but are not limited to:

1. PARP1 Targets for Auto- and Trans-Modification

HAT-Pi treatment competitively inhibits PARP1 at its substrate site inhibiting both trans- and auto-modification. PARP1 auto-modification activity is elevated in neoplastic cells and therefore a logical target of HAT-Pi but trans-modification of other proteins may also contribute to the abnormal behavior of neoplastic cells. PARP1 auto- and trans-modification targets of HAT-Pi include, but are not limited to:

a. Auto-Modification Target-PARP1
Auto-Modification Predominates in Neoplastic Cells.

Multiple sites on the PARP1 protein have been shown to have the potential for auto-modification (S. Vyas, I. Matic, L. Uchima, J. Rood, R. Zaja, R. T. Hay, I. Ahel, C. P. Chang, Nature Communications 5 4426 (2014) and references therein). The known cellular locations of PARP1 enzyme molecules, and therefore those cellular locations where PAR auto-modification may occur, include, but are not limited to chromatin in cell nuclei and nucleoli and the DNA-protein complexes located within mitochondria (W. Mosgoeller, M. Steiner, P. Hozak, E. Penner, J. Wesierska-Gadek, Journal of Cell Science 109 (pt 2) 409 (1996) and references therein).

b. Trans-Modification Targets; Histones and Other Proteins

Trans-modification is the predominate activity of PARP1 in non-neoplastic cells and tissues.

Histones are the most frequent targets for PAR trans-modification consistent with roles in chromatin structure/function. Numerous non-histone proteins have also been shown to be targets of PAR trans-modification and many of these are involved in key cellular processes, including but not limited to: carcinogenesis, inflammation, gene transcription, cell replication and cell metabolism (W. L. Kraus and M. O. Hottiger, Molecular Aspects of Medicine 34 1109 (2013) and references therein).

2. HAT-Pi Inhibition of Other ADP-Ribosylating Enzymes: Potential for Anti-Neoplastic Effects Several other cellular enzymes have $NAD^+$ binding sites which are structurally comparable to the one present in PARP1 and, therefore, these enzymes may potentially be susceptible to HAT inhibition to varying degrees. The enzymes include but are not limited to PARP2 and mono-ADP ribosylating enzymes (Kraus & Hottiger, 2013 op cit and references therein). The effect of HAT-Pi on these enzymes has not been determined, but because the $NAD^+$-binding sites of these enzymes are closely related to that of PARP1, all are likely to be inhibited to some degree by HAT at the dosage levels proposed here. Therefore, anti-neoplastic effects of HAT-Pi may be attributable to inhibition of such other ADP-ribosylating enzymes, and possibly to a lesser or greater extent than the primary target assigned here, namely, PARP1 (poly[ADP-ribose] polymerase 1).

3. Collateral and/or Indirect Consequences of Inhibition of PARP1 Enzymatic Activity Indirect or secondary consequences of the inhibition of PARP1 enzymatic activity may also contribute to its anti-neoplastic effects, including but not limited to:

a) Non-Covalent Binding of Poly[ADP-Ribose] Oligomers/Polymers to Protein and/or Other Molecules The function of cellular proteins may be modified or otherwise influenced through secondary, non-covalent binding to of poly[ADP-ribose] oligomers or polymers that may be free or covalently attached to another, primary modification-target protein (J. P. Gagne, M. Isabelle, K. S. Lo, S. Bourassa, M. J. Hendzel, V. L. Dawson, T. M. Dawson, G. G. Poirier, Nucleic Acids Research 36 6959 (2008) and references therein). Reduction or elimination of such oligomers or polymers of poly[ADP-ribose] through inhibition of PARP1 enzymatic activity may alter the potential for such interactions with unknown consequence(s).

b) $NAD^+$ Depletion and Energy Metabolism $NAD^+$ is an essential coenzyme for oxidative metabolism that is depleted in neoplastic cells and unregulated PARP1 activity is a major contributor to that depletion (Kraus & Hottiger 2013 op cit and references therein). $NAD^+$ depletion may be an underlying reason for the exclusive reliance, in neoplastic cells, on glycolytic metabolism which is less-efficient as a means of energy production than is the oxidative metabolism used by non-neoplastic cells. Inhibition of $NAD^+$ consumption by inhibition of PARP1 enzymatic activity may therefore contribute to HAT-Pi anti-neoplastic effects.

c) HAT-Pi Effects Related to Mitochondria

Although the nucleus is the major site of PARP1 protein and enzymatic activity, PARP1 enzyme molecules are also localized within mitochondria and enzymatic activity of intra-mitochondrial-localized PARP1 has been linked to mitochondrial dysfunction and disease (P. Bai, Molecular Cell 58 947 (2015) and references therein). Inhibition of intra-mitochrondrial PARP1 enzymatic activity may contribute, therefore, to the anti-neoplastic effects of HAT-Pi treatment and may be a potential target in other metabolism-related diseases or conditions including, but not limited to, those involving oxidative stress.

d) HAT-Inhibition of Other Enzymes and Processes

Although HAT-inhibition of PARP1 and ARP family proteins is a predominant effect of HAT-Pi treatment, the activity of other enzymes that are allosterically regulated by thymidine may also be affected by HAT-Pi and which may, therefore, contribute in an unknown manner to the anti-neoplastic effects of HAT-Pi. These include, but are not limited to, various enzymes involved in nucleoside anabolism in cells involved in DNA synthesis (S-phase cells), and dihydrouracil dehydrogenase an enzyme of nucleoside catabolism and production of intracellular signaling molecules.

4. HAT-Pi General Impact on Normal Cells, Tissues and Organs of Patients.

Replicating Cells

Normal cell replication may be largely unaffected by HAT-Pi. HAT-Pi side effects appear to result primarily from inhibition of stem cell replication and/or differentiation, as discussed in more detail in the next section. Adult stem cells, which are replicating cell populations that produce new cells for tissue repair and turnover, comprise a very small proportion of the total number of cells in the adult body.

Non-Replicative Cells and Tissue

A vast majority of body cells never replicate because they are permanently post-mitotic (meaning they have lost the capacity for cell replication). It is unclear at this time what, if any, changes might occur in such cells from inhibition of PARP-1 enzymatic activity at least in comparison to those observed in neoplastic cells for reasons that include, but are not limited to: (a) PARP1 enzymatic activity levels are generally low in non-neoplastic cells; and, (b) trans-modification is the predominant enzymatic activity in which PARP1 is engaged as opposed to auto-modification of PARP1 which predominates in neoplastic cells.

Because the normal cells and tissues of the body are heterogeneous, their responses to HAT-Pi treatment may be expected to be similarly heterogeneous and little information exists to indicate exactly what specific changes may be expected to result from HAT-Pi treatment in each different cell type.

HAT-Pi Toxicity and Side-Effects

HAT-Pi in cell culture is known to inhibit the differentiation of many cell types and induce differentiation of a small number of others. Inhibition of emergence of new, differentiated cells through stem cell activity is a most likely cause of the major side effects of HAT-Pi in human subjects, including but not limited to: myelosuppression (bone marrow. spleen), alopecia (hair follicles), stomatitis (oral mucosa), dermatitis (skin) and diarrhea (gastrointestinal lining). These side effects are reversible upon withdrawal of HAT-Pi and consistent with the generally reversible effects on cell differentiation observed upon HAT-Pi withdrawal in culture. HAT-Pi also has the potential to affect cell differentiation in other tissues and organs in ways that may be deleterious. Side-effect management is considered further in detail below.

1. Potentially Life-Threatening Side-Effects of HAT-Pi

Myelosuppression; a Dose-Limiting Toxicity of HAT-Pi

Myelosuppression observed in historic HAT-Pi patients is consistent with research conducted using experimental animals over 50 years ago showing that HAT reversibly inhibits blood cell development and differentiation (F. Wilt, Proceedings of the National Academy of Sciences USA 48 1582 (1962); R. W. Dutton, J. D. Pearce, Immunology 5 414 (1962) and references therein).

Myelosuppression is the principal dose-limiting-toxicity for HAT-Pi therapy because of its potential to be acutely life-threatening, particularly in patients with one or more debilitating conditions, such as advanced neoplastic disease. Therefore, blood cell count monitoring is a necessary and central parameter of all HAT-Pi treatment strategies and tactics. In brief, nominal "normal" blood cell count values, and potentially tolerable "nadirs" in those blood count values, must be predetermined for each patient prior to initiation of HAT-Pi treatment. Blood cell count "nadirs" establish quantitative criteria for discontinuation of HAT-Pi treatment to prevent irreversible myelosuppression, which could be deleterious and/or life-threatening for that patient.

Blood cell development and differentiation may return during or after an interval of withdrawal from HAT-Pi treatment. When patient blood cell count values return to the pre-determined "normal" levels, it qualifies that patient, in absence of other disqualifying reasons, for resumption of HAT-Pi treatment courses. The return of normal blood cell counts may be the result of renewed replication activity in blood stem cells and the production and differentiation of new blood cells.

The rate of recovery of blood cell differentiation and re-population of various blood cell categories may vary on a patient-by-patient basis. It is essential, therefore, that prior to the onset of HAT-Pi treatment, the decision about what constitutes hematologic 'normal' and 'nadir' values must be taken into account all of the hematologic variables that are important to maintain the patient in good health during the entire HAT-Pi treatment regimen. During patient exposure to HAT-Pi, and regardless of administration route, blood counts must be taken at least twice-per-week to ensure sufficient lead-time to withdraw HAT-Pi treatment prior to blood cell counts falling below the pre-established "nadir'" for that patient.

Twice weekly blood cell count monitoring during scheduled withdrawals of HAT-Pi administration is also important to predict and determine the points at which blood cell counts return to the pre-established 'normal' level for each patient. In one chronic study, involving a regimen of multiple rounds of 14 day continuous infusions of iododeoxyuridine alternating with 14 day recovery periods without infusion, blood cell count returned to normal levels within the first 7-10 days of each.

Because myelosuppression is potentially life-threatening, HAT-Pi treatment should be suspended upon any rapid decline in blood cell count levels irrespective of cause and should not be resumed until blood cell counts have returned to normal levels.

Immunosuppression

The immune response of patients may also be vulnerable to the effects of myelosuppression. HAT treatment has been shown to selectively inhibit the anamnestic antibody response to antigen stimulation (T. F. O'Brien, A. H. Coons, Journal of Experimental Medicine 117 1063 (1963) and references therein), the process by which new antigen recognition and memory are acquired. That finding is consistent with the prediction that patients may experience immunosuppression during HAT-Pi treatment and for a period of unknown duration thereafter. It is strongly recommended therefore that monitoring for immunosuppression be undertaken where appropriate and that HAT-Pi patients are subject to stringent measures to prevent infections or other immune challenge of the type used to protect other immunosuppressed persons.

Familial Pyrimidinemia and Pyrimidinuria

Individuals with inherited deficiency in the enzyme dihydropyrimidine dehydrogenase (H. Ezzeldin, R. Diasio, Clinical Colorectal Cancer 4 181 (2004) and references therein) may catabolize HAT more slowly than normal. Such patients should be subjected to individualized HAT pharmacologic analysis to establish their rate of HAT catabolism prior to receiving HAT-Pi therapy to avoid the potential for HAT over-dosing using the methods outlined herein.

2. Non-Life-Threatening Side-Effects of HAT-Pi

HAT-Pi patients may experience at least one additional side-effect that may be non-life-threatening such as alopecia (hair loss), a common side-effect, and with less frequency stomatitis (mouth sores), dermatitis (skin rash) and/or gastrointestinal disturbance (vomiting and/or diarrhea) (Chang, 1989 op cit and references therein). All of these conditions are most likely due to HAT-Pi-dependent inhibition of stem cell activity and differentiation in these tissues, in a manner similar to inhibition of blood stem cell activity noted above. Although not technically life-threatening, any one of these side-effects may be considered for dose limitation or treatment withdrawal if found to be intolerable to the patient.

3. Teratogenic and Developmental Defects Highly Probable with HAT-Pi

Adult Patients with Reproductive Potential are Ineligible for HAT-Pi

Pregnant persons are not eligible for HAT-Pi because HAT drugs have been shown to be teratogenic in mammals (S. L. Beck, Teratology 47 147 (1993); B. Kolb, B. Pedersen, M. Ballermann, R. Gibb, I. Q. Whishaw, Journal of Neuroscience 19 2337 (1999); and references therein) and, therefore, unborn human exposure at any stage of embryonic or fetal development may result in severe birth defects.

Adult gonadal tissues contain germ cells that differentiate into ova and sperm and support cells that control the development and differentiation of ova and sperm cells. The effects of HAT-Pi on germ cell differentiation have not been determined but there is a strong possibility that birth defects in offspring may result from HAT-Pi-affected germ cells from either parent.

Therefore, adult males must be deemed or surgically-rendered post-reproductive in order to be eligible for HAT-Pi treatment.

Adult females are eligible for HAT-Pi if they are post-menopausal or surgically rendered post-reproductive.

Nursing mothers are not eligible for HAT-Pi, regardless of reproductive status, because HAT may be transmitted by maternal milk and affect infant development, as outlined below.

Children and Young Adults

Extreme caution should be used in evaluating any non-adult patient (infant, child, adolescent or pre-adult) for HAT-Pi therapy due to the high probability for retardation of growth and development of bone, muscle, blood, central nervous system, or other organs and tissues. In younger persons, actively differentiating stem cell populations constitute a far larger proportion of total cells, and, more importantly, anatomically localized stem cell activity is necessary to build tissue and contribute to the growth and function of the organs. HAT-Pi may therefore cause profound inhibition of growth and maturation of multiple tissues, including central nervous system tissues, that may result in severe developmental defects. In addition, reproductive fertility of non-adults is also incompatible with HAT-Pi for the same reasons as it is for adults. Therefore, HAT-Pi is generally not recommended for use in infants, children, adolescents or young adults.

4. HAT-Pi: Unknown and/or Potential Toxicities

Because HAT-Pi is a method for inhibiting enzymatic activity of PARP1, and which broadly inhibits related ARP family enzymes, any biological process that depends upon such activity may potentially be affected. The full range of biological function of PARP1 and other ARP family enzymes is incompletely understood making accurate prediction of all potential side effects impossible. In particular, those side effects that may appear only after extended periods are unknown. Non-limiting examples of potential HAT-Pi toxicities which, although not previously reported, potentially may occur during and after HAT-Pi treatment are:

Potential Toxicity Involving the Central Nervous System

HAT has been shown to impair differentiation and increase cell death in neural progenitor cells (B. Lehner, B. Sandner, J. Marschallinger, C. Lehner, T. Furtner, S. Couillard-Despres, F. J. Rivera, G. Brockhoff, H. C. Bauer, N. Widner, L. Aigner, Cell and Tissue Research 345 313 (2011) and references therein). PARP1 enzymatic activity may be important for multiple aspects of central nervous system function including, but not limited to, gene regulatory processes generally believed to be important in higher neural functions (D. Davar, J. H. Beumer, L. Hamieh, H. Tawbi, Current Medicinal Chemistry 19 3907 (2012) and references therein). The potential exists, therefore, for long-term HAT-Pi treatment to have effects on patient psychic functions including, but not limited to memory formation and/or retrieval. It is therefore prudent and recommended that monitoring, recording and reporting regarding patient higher neural function be conducted during and after HAT-Pi treatment to assess possible effects on memory and consciousness.

Potential Impairment in Tissue Regeneration and Repair

Injury induces stem cell activity to regenerate muscle, bone and other organs. In HAT-Pi patients, such regenerative stem cell activity may be inhibited due to PARP1 inhibition. For example, HAT-Pi-dependent inhibition of muscle stem cells differentiation could affect repair of muscle injury in a patient undergoing HAT-Pi. Repair of other organs and tissues may be similarly impaired through HAT-Pi-dependent inhibition of stem cell differentiation. Therefore, HAT-Pi patients should be protected, and protect themselves, from avoidable damage or injuries to their tissues regardless of cause because such injuries may be improperly or incompletely repaired during, and for an unknown period after HAT-Pi treatment.

Unanticipated Side Effects

PARP1 is intimately involved with genetic control at numerous levels, including but not limited to the formation of transcription initiation complexes at regulatory sites in DNA, the modification of chromosome sub-structure, and the repair of DNA-damage. Inhibition of the activity of this enzyme may, therefore, influence such control in ways that are not yet known and, therefore, may cause unpredicted harm in patients receiving HAT-Pi treatment.

5. Potential DNA-Related Toxicities of HAT-Pi

Because HAT efficiently replaces thymidine during DNA synthesis, and HAT-exposed cultured cells in culture show changes in DNA and/or chromosome structure, these alterations have been generally attributed to the presence of HAT nucleotides in the chromosomal DNA of those cells. Although the incidence of DNA strand breaks and sister chromatid exchanges are increased in HAT-treated cells in culture, PARP1 inhibitors have also been shown to induce similar sister chromatid exchanges (J. L. Schwartz, Chromosoma 93 409 (1986) and references therein). PARP1 inhibitors are also known to increase DNA strand breaks in cultured cells. Therefore, these types of defects may be expected to occur during patient exposure to HAT-Pi therapy but their frequency and consequences are unknown.

III. HAT-Pi: Treatment Implementation

This section provides an outline of methods and rationales for practical implementation of HAT-Pi treatment regimens for advanced neoplastic disease in post-reproductive adult patients, the preferred embodiment.

HAT-Pi for Treatment of Advanced Neoplastic Disease

Introduction

The HAT-Pi procedures and regimens outlined below are intended for treatment of patients with advanced neoplastic disease. Each procedure and regimen is based on clinically-tested protocols published in peer-reviewed medical/scientific journals which have been shown to be effective, in terms of objective and subjective treatment goals, and generally well-tolerated with respect to side-effects.

1. Overview of HAT-Pi Chemotherapy for Advanced Neoplastic Disease

The HAT-Pi Preferred Embodiment is intended for patients with advanced neoplastic disease with or without pain. HAT-Pi chemotherapy calls for chronic exposure of patient plasma and tissue space adjacent to neoplastic tumor cells to one or more HAT chemical compounds at concentrations within a range approximately between 0.1 micromolar and 100 micromolar and with a central target range between 1 and 20 micromolar (as defined above), a concentration range that has been shown to be tolerable and effective in clinical trials with human patients.

Myelosuppression, a potentially life-threatening side effect of HAT-Pi, may be managed by continuous and close monitoring of blood cell counts. In other words, when blood cell counts fall below predetermined "nadir" levels, withdrawal of HAT-Pi administration is indicated and re-administration of HAT-Pi may be resumed when patient blood cell counts have returned to predetermined "normal" levels.

HAT-Pi treatment regimes outlined here suggest strategies and tactics to balance desirable anti-neoplastic effects and undesirable myelosuppression effects. Briefly, the preferred embodiment of HAT-Pi treatment for advanced neoplastic disease includes regular alternating cycles of HAT administration and withdrawal (i.e. complete cessation of HAT administration) to ensure patient myelosuppression recovery prior to receiving additional cycles of HAT-Pi administration.

In other words, a HAT-Pi treatment protocol for an individual patient may include repeated on-off cycles of HAT administration that are designed to prevent myelosuppression from becoming a threat to patient health. Bi-weekly or more frequent assay of blood cell counts are recommended, both during cycles of HAT-Pi administration and during treatment intervals, to ensure that no patient's blood cell counts reach a pre-established nadir and that HAT-Pi treatment be suspended before such a nadir becomes present or imminent.

2. General Qualifications for HAT-Pi Chemotherapy for Advanced Neoplastic Disease General: Post-Reproductive Adult Patients with Advanced Neoplastic Disease objective sign: tumor growth due to uncontrolled tumor cell replication with or without tumor cell metastases.

subjective symptom: existing or anticipation of imminent subjective discomfort, including but not limited to pain, resulting from uncontrolled tumor growth and/or metastases.

life-expectancy: potential patients for HAT-Pi treatment should ideally have a life expectancy of at least 3 months because subjective and objective improvements may require weeks or months to emerge. HAT-Pi treatment in patients with life expectancies of less than three months may not attain all potential treatment benefits.

3. Patient Eligibility: Medical Qualifications for HAT-Pi Treatment

For purposes of qualifying potential patients for HAT-Pi treatment, the following patient eligibility guidelines are based on guidelines used in historic HAT-Pi patients (Table 1) and as reported in Schultz, 2004 op cit and references therein. A complete medical history and physical examination of potential HAT-Pi patients is necessary to establish eligibility according, but not limited to the following criteria:

Performance Status

Karnofsky performance status (KPS, KARNOFSKY PERFORMANCE STATUS SCALE, the entirety of which is incorporated herein by this reference thereto)=60% or higher Eastern Cooperative Oncology Group performance status (ECOG Scale of Performance Status, Eastern Cooperative Oncology Group, the entirety of which is incorporated herein by this reference thereto)=two(2) or lower In other words, a HAT-Pi eligible patient is an adult person who is able to care for most personal needs but may require occasional assistance for daily activities.

Blood Cell Counts

In embodiments, a complete blood count (CBC) for potential HAT-Pi patient to assess bone marrow function is to be performed. To be eligible for HAT-Pi patients may have the following minimum CBC values;

white cells; at least 4000 white blood cells/microliter and/or at least 1,500 neutrophil cells/microliter.

platelets; at least 100,000 platelets/microliter.

Renal Function serum creatinine level; 1.5 milligram/deciliter or less; and/or, creatinine clearance; 60 milliliters/minute or faster.

Liver Function serum bilirubin; less than 1.5 milligram/deciliter;

aspartate aminotransferase; twice the upper limit of normal or lower alanine aminotransferase; twice the upper limit of normal or lower 4. Patient Exclusions and Cautions Patient Exclusions:

Exclusion of prospective patients from the preferred embodiment of HAT-Pi therapy is generally based upon risk factors that include, but are not limited to the following:

Reproductive Risks

Any adult with reproductive competence must be excluded because of teratogenic potential of HAT-Pi therapy. Sterilization or other non-reversible method of birth control is required for these patients to qualify for HAT-Pi therapy.

Developmental Risks

Infants, children, adolescents and young adults are excluded from the preferred embodiment of HAT-Pi treatment because HAT-Pi treatment carries significant risks for debilitating growth and/or other developmental impairment due to inhibition of cell differentiation and tissue growth in developing tissues and organs.

Patient Cautions:

Some patients may be poorly suited for HAT-Pi treatment for reasons that may include but are not limited to;

Prior Chemotherapy or Radiation Therapy

A recovery interval of at least 2 weeks, and ideally a 4-week recovery interval, is recommended prior to initiating HAT-Pi treatment in a patient who has been previously treated by non-HAT-Pi chemotherapy or radiation therapy.

Non-Responsive Neoplastic Cells

HAT-Pi treatment should be withdrawn from any patient with tumor cell types that may not respond to HAT in the manner described here for reasons known or unknown.

Neoplastic Diseases of Blood Cell Lineages

The anti-neoplastic effects of HAT-Pi treatment in patients with leukemia or other neoplastic blood diseases is unclear. HAT inhibits differentiation of some blood-cell-type lineages, such as red blood cells, but HAT may also promote (stimulate) differentiation of other blood-cell-type lineages. That difference may persist among various neoplasms of specific blood-cell-type lineages. Therefore, caution should be observed in the treatment of any patient with blood neoplasms. In particular, prior to consideration of HAT-Pi treatment for blood neoplasms, HAT effects should be tested both in vitro and in vivo to exclude the possibility that HAT may promote replication and differentiation of patient-specific neoplastic cells and thereby exacerbate the disease.

Dihydropyrimidine Dehydrogenase Deficiency

Patients with defects in nucleoside catabolism and elimination may potentially experience higher HAT exposure levels using the HAT-Pi regimens outlined here due to delayed HAT catabolism and resulting accumulation of HAT catabolic intermediates, including but not limited to iodouracil and/or bromouracil, which have potential to inhibit PARP1 enzymatic activity in neoplastic cells. Slower HAT catabolism and elimination in patients with deficiencies in the enzyme dihydropyridine dehydrogenase (DPD) (Ezzeldin & Diasio, 2004 op cit and references therein) could lead to higher doses in such patients. Therefore, to be acceptable for HAT-Pi treatment, a DPD-deficient patient, or any patient with genetic or other defect(s) with the potential to affect HAT metabolism, must be treated with an individualized treatment regimen that includes, in particular but not limited to, ongoing monitoring of HAT pharmacokinetics during HAT-Pi treatment to prevent excessive accumulation of HAT compounds in patient plasma and tissue space and the potential for unpredicted and deleterious effects including, but not limited to; profound and/or life-threatening myelosuppression; and/or unacceptable levels of other side effects.

Unknown but Potential Effects on Fecal Microbiota

HAT-Pi has anti-bacterial effects that may alter fecal microbiota in ways that could render patients more susceptible to pathogens, including but not limited to the bacterium *Clostridium difficile* (M. Agrawal, O. C. Aroniadis, L. J. Brandt, C. Kelly, S. Freeman, C. Surawicz, E. Broussard, N. Stollman, A. Giovanelli, B. Smith, E. Yen, A. Trivedi, L. Hubble, D. Kao, T. Borody, S. Finlayson, A. Ray, R. Smith, Journal of Clinical Gastroenterology Epub 2015).

Side-Effect Intolerance

Additional exclusions include any patient that does not well-tolerate HAT-Pi treatment due to persistence or degree of severity of side-effects or for any other reason that may affect patient health or well-being. For example, some historical HAT-Pi patients were withdrawn from treatment because they experienced a particular side-effect more acutely than others, who were less-affected. The underlying explanations for this type of variability are unknown.

Iododeoxyuridine is Preferred HAT

Iododeoxyuridine is the preferred HAT for use in HAT-Pi treatment for advanced neoplastic disease in human patients. That preference is based upon:

1. Extensive Patient Records

Published reports (see Table 1) document the effects of PARP1-inhibitory-doses of Iododeoxyuridine-alone (in the absence of radiation or other chemotherapy) on scores of human subjects but none indicating that human subjects have been treated with bromodeoxyuridine-alone.

2. Inhibitory Strength Related to Greater Electron Density of Iodine

Iododeoxyuridine has been shown to inhibit PARP1 more strongly than bromodeoxyuridine, probably due to the larger number of electrons in the iodine atom as compared to the bromine atom.

3. Oral Prodrug Potential

An oral prodrug of iododeoxyuridine (5-iodo-2-pyrimidinone-2'-deoxyribose [IPdR; NSC#726188]) has recently been tested in human patients (S. Kummar, L. Anderson, K. Hill, E. Mlajerova, D. Allen, Y. Horneffer, S. P. Ivy, L. Rubenstein, P. Harris, J. H. Doroshow, J. M. Collins, Clinical Cancer Research 19, 1852 (2013) and references therein) and may have reduced side-effects as compared to intravenous iododeoxyuridine. This oral prodrug has potential advantages discussed below.

4. Bromodeoxyuridine; Potential Uses

Because bromodeoxyuridine may be slightly weaker in inhibition of PARP1 enzymatic activity than is iododeoxyuridine it has potential to serve either as an alternate to or in combination with the former or its prodrug.

Symptom Status: Record Keeping and Evaluation

1. Symptom Improvement; a Primary Objective

Symptom relief is a primary objective of HAT-Pi treatment as a treatment alternative to the exclusive or predominant usage of opioids to treat pain in patients with advanced neoplastic disease. Because the mechanisms responsible for HAT-Pi symptom-relief differ from those responsible for opioid-based symptom-relief it is potentially possible to employ both simultaneously during HAT-Pi treatment regimens in order to progressively reduce the level of opioid usage.

Daily symptom records are intended to closely track the subjective experience of the patient with respect to use of other non-HAT pain-relief medication or methods that may occur concurrently with HAT administration. That record provides a measure of the role and efficacy of HAT as a mediator of symptom-relief on a patient-by-patient basis.

Daily symptom-records also have potential prognostic value, subjectively for the patient and, possibly, objectively with regards to the prospects of tumor regression and/or reduction of metastases, both of which lagged subjective improvement in Patient One (see FIG. 3A).

2. Symptom Monitoring as a Means to Subjectively Evaluate HAT-Pi Efficacy

The symptom monitoring strategy for HAT-Pi is based upon the treatment records of the first HAT-Pi patient (FIG. 3A) in which daily subjective symptom records were reported. No comparable symptom records were published for subsequent patients that received HAT. That record demonstrates the temporal coincidence of the onset of pain relief and myelosuppression after a period of HAT exposure. In her case, each pain relief period persisted longer than the corresponding period of myelosuppression.

Daily subjective symptom reports, combined with bi-weekly blood cell counts, comprise a unique record of HAT-Pi treatment progress which has prognostic potential and that can be followed and evaluated by the patient.

3. Symptom Daily Evaluation Reports Composition:

Subjective Assessment of Symptoms

The subjective measurement comprises daily self-assessment by the HAT-Pi patient of her/his experience of "pain" (or other discomfort) and/or feelings of "well-being" on a simple quantitative scale (such as, but not limited to: a 0-10 scale, with '0' designating complete absence of any discomfort or pain; and '10' designating the worst pain or discomfort imaginable by the patient, and numbers in between representing a step-gradient between those two extremes).

Objective Assessment of Symptoms

The objective measurement comprises quantified contemporaneous usage of other symptom-relieving medication including, but not limited to; non-prescription analgesic usage (over the counter drugs such as, but not limited to aspirin, ibuprofen and/or acetaminophen), prescription analgesic usage (i.e. prescription drugs such as, but not limited to natural and synthetic opioids), prescription sleeping medication usage and/or any other objective/external assessment(s) of patient experience of pain and/or feelings of well-being that may be deemed appropriate.

4. Symptom-Relief may be a Leading Indicator of HAT-Pi Efficacy

A quantitative decrease in patient-reported symptoms and/or decreased usage of pain-relieving medication may provide a measure of HAT-Pi efficacy that is accessible, on an ongoing basis, for subjective and objective assessment of the HAT-Pi treatment regimen employed.

5. Patient Symptom Relief Experience and Anti-Neoplastic Tumor Cell Correlates

Many days or weeks of HAT-Pi treatment may be necessary for a patient who has already been experiencing neoplastic disease-related pain to begin to experience the onset of symptom relief. FIG. 3A also illustrates that the onset of symptom relief may provide the first evidence that chronic HAT-Pi treatment is beginning to have anti-neoplastic effects. On a cellular level these anti-neoplastic effects include, but may not be limited to:

Tumor Cell Arrest replication arrest, contact inhibition, metastasis arrest slow or stop the growth pressure from tumor expansion; and Tumor Cell Disintegration death and disintegration of unattached tumor cells and induced autonomous mechanisms of tumor cell death lead to reduction in mass of tumor cells further reducing pressure of tumor tissue on normal tissues.

6. Reversibility of Symptom Relief

The record of Patient One (FIG. 3A) illustrates the reversibility of symptom relief from HAT-Pi and that maintaining symptom relief is likely to require continued, repeated courses of HAT-Pi exposure over a treatment period of 23 or more weeks. Although some historic HAT-Pi patients were reported to have experienced persistent symptom relief for extended periods after cessation of HAT-Pi treatment, systematic information is not available at this time that can predict the durability of symptom relief after an extended period of HAT-Pi treatment.

7. HAT-Pi Non-Responsive Patients

An unknown proportion of patients with neoplastic disease may not experience symptom relief as a result of HAT-Pi treatment. Such non-responsive patients may include those with tumors which are: a) too highly aggressive or too highly advanced to be overcome by HAT-Pi treatment; b) comprised of cancer cell types that are intrinsically HAT-unresponsive because their behavior is independent of PARP1 enzymatic activity for unknown reasons; and/or c) other unknown reasons.

HAT-Pi Toxicity Monitoring and Management

Introduction

Tolerance of HAT-Pi side-effects varies on a patient-by-patient basis and, therefore, monitoring and management of HAT-Pi side-effects must also be tailored to the individual patient needs and conditions. Concentrated attention towards HAT-Pi effects on blood-forming activity is of primary importance because of the potential life-threatening consequences of uncontrolled myelosuppression.

Hematology Monitoring to Manage Myelosuppression

HAT-Pi inhibits blood cell differentiation. A full hematology analysis (complete blood cell counts and serum chemistry) should be performed prior to administration of HAT-Pi treatment.

Hematology Twice Per Week

During a HAT-Pi treatment regimen, hematologic evaluation should be conducted twice per week, or more frequently, to monitor and record the rate of (expected) progressive myelosuppression during periods of HAT administration. Continued bi-weekly hematologic evaluation during scheduled intervening periods, when HAT is not being administered, are important to monitor and record the rate of recovery from myelosuppression.

HAT-Pi Treatment Withdrawal in Hematological Emergency

The treatment regimens outlined in a subsequent section involve repeated cycles of HAT administration with intervening periods of no HAT administration that are intended to maintain acceptable blood cell counts throughout both periods. However, these regimens may not be suitable for all patients and therefore close hematologic monitoring is important to inform a decision to withdraw administration of HAT-Pi prior any unexpected or precipitous decline in hematology values that could potentially threaten patient health or life. Re-administering HAT-Pi treatment after such an "emergency withdrawal" requires that hematologic values have returned to acceptable levels for that patient.

Toxicity Limits

Hematologic toxicity is universally experienced in HAT-Pi treatment regimens that is potentially life-threatening and must be managed accordingly. The following criteria are suggested regarding the predictability of myelosuppression nadirs during a HAT-Pi treatment regimen and/or timing of withdrawal of HAT-Pi in anticipation of hematologic emergency. Each of the suggestions must be evaluated in context of overall patient health.

Myelosuppression Nadir: Guideline Criteria for HAT-Pi Treatment Withdrawal

HAT-Pi inhibits blood cell development. Anticipation of this toxicity is a central aspect of any HAT-Pi treatment regimen. Myelosuppression is HAT-dose-dependent and, as a general rule, the onset may be more rapid in patients receiving doses of HAT in the higher ranges than those receiving doses in the lower range. The effects of myelosuppression by HAT-Pi progress and appear in a time-dependant fashion and nadir values establish boundaries for HAT-Pi treatment withdrawal.

The following guidelines for the withdrawing HAT-Pi due to myelosuppression are broadly based on guidelines developed at the United States National Cancer Institute (Kummar, 2013 op cit and references therein).

Suspension or interruption of HAT-Pi treatment may be indicated if hematologic analyses indicate one or more of the following clinical toxicities, as defined by Common Terminology Criteria for Adverse Events (CTCAE, v. 4.3 2010, the entirety of which is incorporated herein by this reference thereto):

grade 2 or higher thromobocytopenia,
grade 3 or higher anemia,
grade 3 or higher leucopenia,
grade 3 or higher neutropenia.

Timing of Myelosuppression Nadirs in Designing a HAT-Pi Treatment Regimen

In an ideal HAT-Pi treatment regimen the patient does not experience myelosuppression nadirs due to the scheduled withdrawal. Nevertheless, HAT-Pi treatment is to be withdrawn should bi-weekly hematologic examinations predict the appearance of an unexpected myelosuppression nadir.

Timing of Myelosuppression Recovery

Restoration of marrow function and a return to normal blood count levels may be expected to occur in most patients within one to two weeks after withdrawal of HAT-Pi treatment. Restoration of normal blood count values is a condition for patient qualification for resuming HAT-Pi treatment cycles.

Monitoring and managing of HAT-Pi non-hematologic-side effects

Source and Variability of HAT-Pi Side-Effects

Other side-effects of HAT-Pi treatment include, but are not limited to: alopecia, dermatitis, diarrhea or other gastrointestinal disturbance, and stomatitis, and may also be due to the suppression of normal cell differentiation in various tissues and organs. These HAT-Pi side-effects are generally non-life-threatening and, on a patient-by-patient basis, may be variable in both appearance and/or severity. Any one of these, however, may prove to be dose-limiting in an individual patient.

Grade 2 Toxicity

Any non-hematologic grade 2 toxicity (other than correctable electrolyte imbalances), may, in consultation with patient perception and wishes, be considered as sufficient reason to withdraw or modify HAT-Pi treatment regimens.

Suggested HAT-Pi Treatment Regimens for Patients with Advanced Neoplastic Disease HAT-Pi treatment regimens outlined here are based on previously published regimens for HAT administration that were employed to treat the historic HAT-Pi patients (see Table 1). In those clinical trials and pharmacological analyses, however, the goal was to maximize synthesis of HAT-DNA, not HAT-Pi. This section, therefore, begins with an outline review of the goals, rationales and strategies that are the basis for HAT-Pi treatment regimens outlined below.

1. Review of HAT-Pi Treatment Concepts

HAT-Pi Treatment Goals

The goals of HAT-Pi treatment are to provide subjective and objective improvement in patients with advanced neoplastic disease by the arrest of neoplastic tumor cell replication and metastases, and through tumor regression resulting from neoplastic tumor cell disintegration by autonomous cell death processes.

HAT-Pi Treatment Strategy

The treatment strategy is to expose neoplastic tumor cells to HAT at concentrations in excess of 1.0 (one) micromolar with the purpose of partially or completely inhibiting PARP1 enzymatic activity in neoplastic tumor cells.

HAT-Pi Treatment Biological Basis

HAT inhibition of PARP1 enzymatic activity leads to the arrest of uncontrolled replication and migration of neoplastic tumor cells. In cell culture, most but not all neoplastic cells disintegrate and die within 2 weeks of HAT-Pi treatment but the rate of neoplastic tumor cell disintegration in vivo is unknown and may vary on a patient to patient basis.

HAT-Pi Myelosuppression

HAT-Pi treatment also results in myelosuppression, a potentially life-threatening side-effect of HAT-Pi, which necessitates periodic withdrawal of HAT-Pi administration to allow for recovery of blood cell-forming capacity in patients. Close monitoring of patient hematologic status is a central and guiding principle of HAT-Pi treatment regimens.

2. HAT-Pi Treatment Regimen: ON-OFF Cycling of HAT-Exposure

The treatment effects and side effects of HAT-Pi treatment are reversible after treatment is withdrawn. The repeated on-off cycles of HAT-Pi treatment courses are intended to:

a) Manage Myelosuppression

A full regimen of HAT-Pi treatment for patients with advanced neoplastic disease covers a period of approximately 5 months and comprises multiple courses of HAT-infusion interspersed with periods of no HAT infusion. The intended purpose of interspersed periods of no HAT infusion is to allow for recovery from myelosuppression which is the principal and potentially life-threatening side effect of HAT-Pi treatment. Management of myelosuppression is therefore a key aspect of any HAT-Pi treatment regimen and, over a 5 month treatment period, patient hematological status must be carefully considered with respect to; a) the rate and extent of recovery after each HAT-infusion course; and, b) quantitative evaluation of the full spectrum of cellular and other components of the patient circulation and with respect to the patient response to HAT-Pi treatment in context of overall patient health.

In other words, continuous monitoring of blood cell counts (at least twice per week) is necessary to anticipate the need to withdraw HAT infusion prior to patient blood counts reaching a pre-determined nadir. In addition, the rate of myelosuppression may vary from one HAT infusion cycle to another and the myelosuppression recovery rate may also vary from one cycle to the next. It is therefore necessary to continuously monitor this parameter at least twice per week or even more frequently to protect patient health during any HAT-Pi treatment regimen. Re-initiation of HAT infusion is dependent in all instances upon patient blood cell count values having returned to values consistent with the pre-determined "normal" value.

b) Impose Repeated Waves of Neoplastic Tumor Cell Arrest and Disintegration

The gaps in HAT-Pi treatment may also potentially allow neoplastic tumor cells that may have begun to recover from the effects of inhibition of PARP1 enzymatic activity to resume uncontrolled cell replication and uncontrolled cell movements associated with metastases. Repeated courses of HAT-Pi treatment according to the treatment regimens outlined below therefore serially re-impose inhibition of PARP1 enzymatic activity and re-arrest such neoplastic tumor cells and to progressively cause their further disintegration and death.

3. Administration Routes for HAT-Pi

HAT-Pi treatment for patients with advanced neoplastic disease calls for exposing neoplastic tumor cells to iododeoxyuridine (a HAT) at concentrations approaching or in excess of 1.0 micromolar. This has been achieved in historical HAT-Pi trials through multiple routes of administration including but not limited to:

Circulatory Infusion

Circulatory infusion exposes virtually all tissues and cells, including neoplastic cells, to HAT-Pi. Circulating HAT at concentrations in excess of 1.0 micromolar in human patients has been maintained by controlled infusion of concentrated HAT buffered solutions directly into the blood stream through a vein (iv) or artery (ia), which is sustainable 24/7 over periods of multiple weeks;

Intraperitoneal Infusion

Infusion of a concentrated solution of HAT into the peritoneal cavity may be used to expose neoplastic tumor cells in organs that are either within, and/or anatomically-associated with the peritoneal cavity to be exposed to HAT concentrations exceeding 1.0 micromolar;

Oral Tablet

Ingestion of an oral tablet containing a HAT prodrug has potential to become a simpler method of HAT-Pi treatment because it has been demonstrated to attain circulating plasma of HAT concentrations in excess of 1.0 micromolar during short-term exposure. That HAT prodrug, however, by oral ingestion has yet to demonstrate the maintenance of HAT concentrations in excess of 1.0 micromolar continuously over periods of multiple weeks nor has it yet been shown to be effective for treatment of advanced neoplastic disease; and Focal Application Localized exposure of tumor cells and/or tissues to HAT at concentrations in excess of 1.0 micromolar may also be achieved by focal application, such as directly into a ventricle of the brain, by intrathecal injection, for one non-limiting example, which may result in concentrated HAT exposure to neoplastic tumor cells located within associated central nervous system tissues. Other focal applications may also be considered.

4. HAT-Pi Circulatory Infusion

Figure 5A:
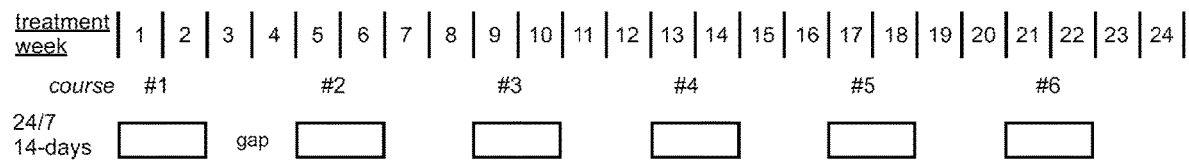
FIGS. 5 A-C provide diagrams illustrating suggested HAT-Pi treatment regimens.

The protocols and schedules for HAT-Pi infusion regimens outlined below and illustrated in FIG. 5A are based on HAT administration regimens that have been previously tested in clinical studies of human subjects (see Table 1 and FIG. 3).

Routes for Circulatory Infusion

The decision regarding administration route of HAT-Pi therapy must be chosen individually for each patient. In embodiments, the choice may be made for infusion via the intravenous route, because of its relative simplicity and convenience, and because HAT infusion via the intravenous route has been demonstrated to maintain steady-state plasma HAT concentrations in excess of 1.0 micromolar on a 24/7 basis over multiple weeks. Importantly, subjective improvement has specifically been reported for patients receiving HAT via circulatory infusion.

Intra-arterial infusion of HAT is a potential alternative circulatory infusion route which may be indicated for some patients and/or types of neoplastic disease. Intra-arterial infusion may have a higher rate of infusion site failure. In addition, for arterial infusion, HAT infusion solution concentrations must be individually calibrated for each patient to prevent potential adverse effects on target tissues and organs that may result from excessive HAT concentration in tissue space served by capillary fields of the injected artery.

Prospective Patients for HAT-Pi by Circulatory Infusion

Prospective patients for circulatory infusion are those having advanced neoplastic disease in organs, tissues and tissue-spaces that may be exposed to HAT present in circulating plasma (serum) and who meet the other criteria for HAT-Pi treatment outlined above.

HAT Stock Solutions for Circulatory Infusion

Sterilized powder consisting of crystals of HAT (iododeoxyuridine in preferred embodiment) may be dissolved in sterile, physiologically-buffered solution suitable for intravenous infusion according to the schedules in Table 2.

Circulatory Infusion Dosage Schedules

A goal of the HAT-Pi treatment for advanced neoplastic disease by circulatory infusion is to achieve patient steady-state plasma levels of HAT (iododeoxyuridine or bromodeoxyuridine) at concentrations in excess of one (1.0) micromolar and to maintain that concentration level for extended periods. This may be achieved by circulatory infusion through daily bolus injections, or continuous infusion for 12-hours per day, or by continuous 24-hour/day infusion over periods of weeks. Table 2 shows non-limiting examples of circulatory infusion rate schedules that have been reported to achieve HAT concentrations in patient serum that approach or exceed one (1.0) micromolar sufficient to exert partial or complete inhibition of PARP1 enzymatic activity in exposed neoplastic cells.

TABLE 2

Iododeoxyuridine dose versus circulating plasma concentrations suitable for HAT-Pi

| schedule | Route of Infusion* | Amount infused Grams/M$^2$/day | [IdU] plasma# (micromolar) | [IU] plasma# (micromolar) | reference |
|---|---|---|---|---|---|
| A | 2 hr bolus iv | 3.1 | NR | NR | Calabresi, 1961 op cit |
| B | Continuous ia | 1.300 | NR | NR | Chang, 1989 op cit |
| C | Continuous iv | 1.200 | 7.4 | NR | Klecker, 1985 op cit |
| D | Continuous iv | 1.200 | 3.4 | NR | Kinsella, 1988 op cit |
| E | Continuous iv | 1.000 | 5.6 | NR | Klecker, 1985 op cit |
| F | Continuous iv | 1.000 | NR | NR | Chang, 1989 op cit |
| G | Continuous iv | 1.000 | 2.4 | >20 | Kinsella, 1988 op cit |
| H | Continuous iv | 0.850 | 4.5 | NR | Klecker, 1985 op cit |
| I | Continuous iv | 0.781 | 1.5 | 21.8 | Schultz, 2004 op cit |
| J | Continuous iv | 0.625 | 1.3 | 13.9 | Schultz, 2004 op cit |
| K | Continuous iv | 0.500 | 2.9 | NR | Klecker, 1985 op cit |
| L | Continuous iv | 0.500 | 1.3 | NR | Kinsella, 1988 op cit |
| M | Continuous iv | 0.500 | 0.92 | 6.0 | Schultz, 2004 op cit |
| N | Continuous iv | 0.400 | 0.90 | 4.3 | Schultz, 2004 op cit |
| O | Continuous iv | 0.300 | 0.57 | 3.0 | Schultz, 2004 op cit |
| P | Continuous iv | 0.250 | 1.1 | NR | Klecker, 1985 op cit |
| Q | Continuous iv | 0.200 | 0.79 | 1.4 | Schultz, 2004 op cit |
| R | Continuous iv | 0.100 | 0.51 | 0.38 | Schultz, 2004 op cit |

*Continuous infusions periods spanned either 12 hours/day or 24 hours/day.
[IdU] and [IU] indicate average steady-state plasma concentrations of these two HAT molecules in patients undergoing circulatory infusion of iododeoxyuridine (IdU).
NR—not reported New Patients; Introduction to HAT-Pi Circulatory Infusion.

When possible, to assess drug tolerance, new or prospective HAT-Pi patients may first be given trial infusions over several days using HAT infusion in the low concentration ranges. HAT intolerance, if experienced, may include, but may not be limited to; nausea, diarrhea, or skin rash. If HAT intravenous infusion is well-tolerated at low concentrations then infusion of higher concentrations of HAT may be reasonably considered for long-term and repeated treatment courses outlined below.

HAT-Pi 14-Day Circulatory Infusion Regimen; (FIG. 5A)

FIG. 5A illustrates a HAT-Pi treatment regimen that consists of repeated 14-day-long courses of continuous (24/7) intravenous infusion of iododeoxyuridine (or other HAT) interspersed by gaps of 14-day-long periods without HAT infusion. HAT infusion rate schedules are shown in Table 2 that have been demonstrated to maintain continuous circulating HAT steady-state plasma concentrations approaching or in excess of one (1.0) micromolar.

Employing the schedule outlined above and illustrated in FIG. 5A, both the occurrence of myelosuppression nadirs and recovery to normal blood cell counts, were reported to have occurred within the first 7-10 days after scheduled HAT-withdrawal. In other words, the 2-week period between HAT infusions segments was usually long enough for adequate myelosuppression recovery, as illustrated in FIG. 5A. That is also consistent with the conclusion that only on rare occasion did results of ongoing bi-weekly hematology testing provoke an unscheduled cessation of HAT infusion that would have been indicated if patient blood cell counts had approached a pre-determined blood cell count nadir.

Additional details regarding the pharmacology, toxicity and efficacy of the 2-week HAT-Pi infusion regimen may be found in Chang et al, 1989 op cit, Kinsella, 1987 op cit, and in references therein.

HAT-Pi 28-Day Circulatory Infusion Regimen;

HAT steady-state concentrations in patient plasma in excess of one (1.0) micromolar have also been maintained in patients during a single 28-day-long course of circulatory HAT infusion at rates (Schultz, 2004 op cit). No report is available on the pharmacokinetic or toxicology effects that may result from multiple, repeated 28-day infusion courses over extended periods, such as proposed here for HAT-Pi. Extended HAT-Pi exposure times, by extending the duration of neoplastic cell arrest, may lead to increased neoplastic tumor cell death and disintegration during each treatment course and its aftermath.

HAT-Pi by Bolus Infusion

Bolus injection is a potential alternative method of administering HAT-Pi treatment if continuous infusion is not possible or is undesirable. Daily 2-hour bolus infusions of up to 3.75 grams/meter$^2$ were administered to the first historic HAT-Pi patient (FIG. 3A). Such high doses may be poorly tolerated by some patients. In addition, after bolus infusion, HAT plasma concentrations continuously decline over 24 hours to concentrations below the 1.0 (one) micromolar level due to elimination through hepatic and renal metabolism. Nevertheless, the relative efficacy of HAT-Pi treatment by bolus versus continuous infusion is undetermined.

Dose Reductions

Reductions in the level or duration of HAT dosages, and with resulting reduction in plasma/tissue-space concentration targets, may be considered under circumstances including but not limited to those in which:

a) a lower HAT concentration is found to be sufficient for maintaining (as opposed to initially establishing) inhibition of PARP1 enzymatic activity;

b) less-advanced neoplastic disease is found to be responsive to HAT-Pi treatments employing lower HAT concentrations;

c) repeated treatment and/or long-term HAT-Pi treatment maintenance for individuals who have already undergone at least one full HAT-Pi treatment regimen, as above; and d) a patient with low-HAT-tolerance in which HAT-Pi treatment is administered in a manner that leads to plasma concentrations of HAT at sub-micromolar concentrations proves partially or fully effective in palliation or objective improvement or both.

5. HAT-Pi Peritoneal Infusion

Peritoneal infusion is an alternative route of HAT administration for patients having neoplastic disease within organs and/or tissues that are closely associated with the abdominal cavity including, but not limited to: digestive tract and associated organs such as liver, gall bladder and pancreas; non-digestive-tract organs such as spleen, kidney, uterus, ovaries urinary bladder, prostate, and body wall structures and membranes; and, nervous system-related-tissues such as nerve cells, ganglion cells, and adrenal gland. Intraperitoneal HAT-Pi infusion involves transient (4 hour/day) exposure of peritoneum-associated organs to HAT concentrations in the millimolar range and slower adsorption of HAT into the circulating plasma. Reduced circulatory exposure may, to an unknown extent, lessen the potentially deleterious side-effects, such as myelosuppression, as one non-limiting example, which may result from extended exposure of bone marrow to high-concentrations of HAT.

Prospective Patients for HAT-Pi by Intraperitoneal Infusion

Prospective patients for HAT-Pi by intraperitoneal infusion are those with advanced neoplastic disease in intraperitoneal organs and tissues and/or retro-peritoneal organs and tissues in close anatomical association with the peritoneal cavity and who meet the other criteria for HAT-Pi treatment outlined above.

HAT Stock Solutions for Intraperitoneal Infusion

Sterilized powder consisting of crystals of HAT (iododeoxyuridine in preferred embodiment) are dissolved in two liters of sterile physiological saline suitable for intraperitoneal infusion. One intraperitoneal infusion dose comprises a sterile 2-liter infusion volume containing HAT in the amounts shown in Table 3. Infusion duration is 4 hours with periodic position changes to optimize organ exposure, after which the solution containing HAT is removed.

TABLE 3 iododeoxyuridine concentrations suitable for HAT-Pi by intraperitoneal infusion;

| schedule | Grams/M$^2$/ 4 hr (2 liters) | HAT concentration in infusion solution | Peritoneal AUC* (µM × hr) | Plasma AUC* (µM × hr) |
|---|---|---|---|---|
| A | 4.538 | 64 millimolar | 4099 | 139 |
| B | 4.125 | 59 millimolar | NR | NR |
| C | 3.750 | 53 millimolar | NR | NR |
| D | 2.500 | 35 millimolar | NR | NR |
| E | 1.250 | 18 millimolar | NR | NR |
| F | 0.625 | 9 millimolar | NR | 4.38 |

*AUC; area under the curve, expressed as micromolar concentration times hours of exposure (M × h), is a measure of transient exposure only during the 4-hour infusion period. The values shown are averages from multiple patients as reported in Morgan, 1998 op cit. NR; not reported.

New Patients: Introduction to HAT-Pi Peritoneal Infusion

When possible, new or prospective HAT-Pi patients should first be given peritoneal infusions with low HAT concentrations over several days to experience HAT plasma concentrations in the lowest HAT-Pi ranges and to assess drug tolerance. HAT intolerance, if experienced by the patient, may include, but is not limited to: nausea, diarrhea, or skin rash. If HAT peritoneal infusion is well tolerated at low HAT concentrations then infusion of higher concentrations of HAT (e.g. ip rate schedules A-C, Table 3) may be reasonably considered for the longer term treatment regimens outlined below.

Figure 5B:
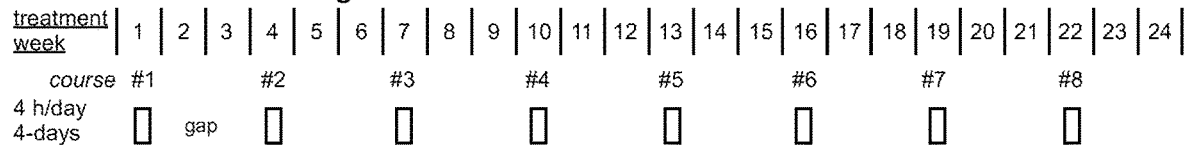

HAT-Pi Peritoneal Infusion Regimen (FIG. 5B)

FIG. 5B illustrates a treatment regimen for HAT-Pi administered by intraperitoneal infusion. The pharmacology and toxicology of peritoneum-infused HAT at doses shown in Table 3 given patients having advanced neoplastic disease has been reported (Morgan, 1998 op cit and references therein).

6. Potential HAT-Pi Oral Dosing

Figure 4D:
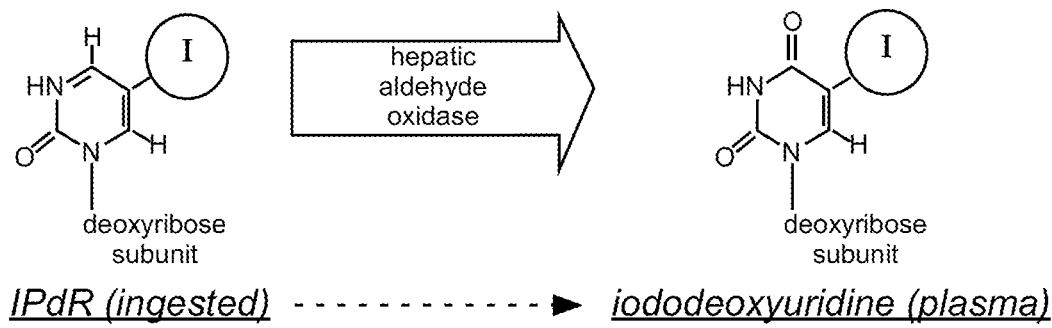

A potential alternative method of administering HAT-Pi is by using IPdR (5-iodo-2-pyrimidinone-2'-deoxyribose) a HAT pro-drug that can be administered orally. Ingested IPdR is converted in the liver by the enzyme hepatic aldehyde oxidase and released into the plasma as iododeoxyuridine, an active form of HAT (FIG. 4D).

Prospective Patients for HAT-Pi by Oral Ingestion

Prospective patients for HAT-Pi by oral ingestion are those having advanced neoplastic disease who meet the other criteria for HAT-Pi treatment outlined above.

IPdR Dose Schedules

Table 4 lists average peak concentrations of iododeoxyuridine (HAT) in patient plasma within 2 hours after administration of a single oral dose of IPdR (S. Kummar (2013) op cit and references therein). HAT concentrations declined rapidly over the ensuing 12-hour period.

TABLE 4

HAT plasma concentrations resulting from oral dosing with IPdR tablets

| schedule | Grams IPdr Per $M^2$/day | [IdU] plasma micro molar | IdU AUC μM × h | [IU] micro-molar | IU AUC μM × h |
|---|---|---|---|---|---|
| A | 2.40 | 4.0 | 12.2 | 133 | 1057.8 |
| B | 1.20 | 2.1 | 4.7 | 34.2 | 102.7 |
| C | 0.60 | 1.8 | 3.2 | 4.5 | 17.2 |
| D | 0.30 | 0.3 | 0.3 | 0.8 | 4.5 |
| E | 0.15 | 0.8 | 1.7 | 0.2 | 1.0 |

[IdU] plasma and [IU] plasma are the average maximum concentration values in patient plasma of are iododeoxyuridine and iodouracil, respectively. Other abbreviations as in Table 3. The values shown averages from multiple patients as reported in Kummar, 2013 op cit.

New Patients: Introduction to HAT-Pi Dosing by Oral Tablets of IPdR

When possible, new or prospective HAT-Pi patients should first be given IPdR tablets containing relatively low doses (for example, rate schedules C-E, in Table 4) to experience HAT plasma concentrations in the lowest HAT-Pi ranges to assess drug tolerance. HAT intolerance, if experienced, may include, but may not be limited to: nausea, diarrhea, or skin rash. If IPdR oral dosing is well tolerated at these concentrations then infusion of higher concentrations of HAT (for example, rate schedules A or B, in Table 4) may then be reasonably considered for long-term and repeated treatment courses outlined below.

HAT-Pi Potential Oral Dosing Regimen; (FIG. 5C)

No studies of the oral mode of administration of IPdR have been reported that involved multiple, repeated doses given over an extended period as proposed for HAT-Pi. This proposed regimen for oral IPdR treatment is therefore presented only for illustration purposes. A usable treatment regimen for HAT-Pi using IPdR is dependent upon more extensive pharmacology, toxicology and efficacy studies in human subjects.

Figure 5C:
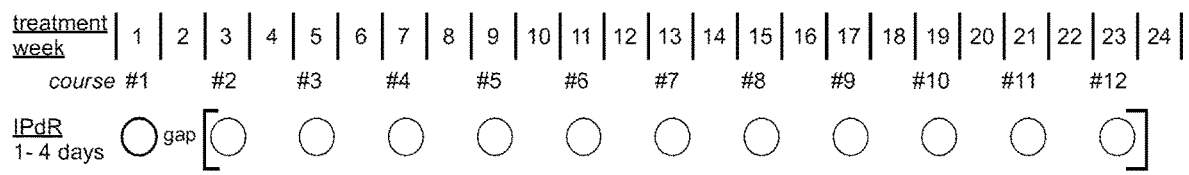

FIG. 5C illustrates one possible treatment regimen for HAT-Pi administered using tablets of IPdR that is adapted from reports of phase 0 (pharmacologic) studies in patients who were administered only one oral dose and then clinically followed for 14 days (Kummar, 2013 op cit).

7. Summary and Comparison of Maximum HAT Dosages

Patient tolerance of HAT doses may depend upon the route of administration. Table 5 shows the maximum HAT dose per day administered by the three administration routes outlined above and the resulting maximum plasma concentration of iododeoxyuridine and iodouridine measured in patients receiving those doses. The suitability of HAT dosages in excess of those listed in Table 5 has not been determined.

TABLE 5

Maximum HAT doses that have been clinically evaluated

| Route of HAT administration | HAT dose/day Maximum | Exposure cycle Length in Days | HAT total dose/ cycle | max Idu plasma (micromolar) |
|---|---|---|---|---|
| circulatory | 1.2 grams/$m^2$ | 24 h/day × 14 | 168 grams | 7.4 steady state |
| intraperitoneal | 4.5 grams/$m^2$ | 4 h/day × 4 | 18 grams | 139 AUC-4 h |
| oral | 2.4 grams/$m^2$ | 1 time only | 2.4 grams | 4.0 peak value |

[Idu], concentration of iododeoxyuridine. Other abbreviations as in Table 3.

IV. Adaptive HAT-Pi Treatment Guidelines.

Modification of the Preferred Embodiment for HAT-Pi treatment conditions for advanced neoplastic disease outlined in the previous section may be considered under various circumstances, including but not limited to: a) if a patient poorly-tolerates HAT-Pi side-effects during an initial course of HAT-Pi treatment; b) if a patient has recurring signs and symptoms of neoplastic disease after completing a full regimen of HAT-Pi treatment; and/or c) if a patient with less-than-advanced neoplastic disease is being considered for treatment with HAT-Pi.

HAT-Pi treatment modification may also be undertaken with the purpose of adapting HAT-Pi treatment for any other disease or condition in which inhibition of the enzymatic activity of PARP1 may have therapeutic benefit (Kraus, 2013 op cit; C. Hegedus, L. Virag, Redox Biology 2C 978 (2014); K. Modis, D. Gero, K. Erdelyi, P. Szoleczky, D. DeWitt, C. Szabo, Biochemical Pharmacology 83 633 (2012); and references therein) and including unspecified conditions or diseases that may presently be unknown.

Situations calling for adaptive changes in HAT-Pi treatment regimens include, but are not limited to:

1. Subsequent HAT-Pi Regimens in Patients Previously Treated by a Full HAT-Pi Regimen.

Neither the anti-neoplastic efficacy nor the toxic side effects of repeated HAT-Pi treatment regimens have been studied in human patients. The potential exists for irreversible effects on the regenerative capacity of blood and other stem cells after repeated HAT-Pi treatment is unknown. Therefore, re-calibration of HAT dose, duration of exposure and side-effect management must be undertaken in such cases.

2. Alternate Administration Routes for Neoplastic Disease.

Anatomically-localized neoplastic diseases may be targeted by localized HAT-Pi administration. In these cases, as with intra-arterial infusion discussed above, careful consideration must be given to the concentration of the HAT solutions used to avoid excessive HAT exposure levels.

Site-Localized Injection

Localized infusion is intended to concentrate HAT-Pi treatment to neoplastic tumor cells that may be located within a large tumor mass or neoplastic tumor cells associated with any anatomically-defined space or cavity into which a concentrated HAT solution can be injected including, but not limited to cavities contained within the: central nervous system (brain ventricles and spinal cord central canal), meningeal layers of the central nervous system (arachnoid spaces between pia and dura mater, dural sinuses), eyes, ears, sinuses, nose and mouth, pharynx and larynx, primary digestive tract, pleura, lung, liver, gall bladder, urinary tract, reproductive tract, marrow cavities of bones or other hollow organs or tissue spaces.

Superficial Salves

HAT drugs administered to the body surface as an ointment/salve may expose epidermis, dermis and, potentially, associated underlying tissues to the antineoplastic effects of HAT-Pi.

3. Alternative HAT Dosing Regimens for Neoplastic Disease

Combinatorial Dosing with Non-HAT Inhibitors of PARP1 Enzymatic Activity

Modified HAT-Pi treatment regimens may combine HAT with other inhibitors of PARP1 enzymatic activity that are chemically unrelated to HAT. In embodiments, other non-HAT PARP1 inhibitors that may be used in combination with HAT:

a) may have distinctive chemical or other properties that may prolong inhibition of PARP1 enzymatic activity in neoplastic tumor cells; and/or b) may act through binding to an inhibitory site or sites within the PARP1 protein that is/are distinct from the $NAD^+$-binding site. The 1st zinc finger of PARP1 is one potential and non-limiting example of an alternative inhibitory site. Zinc finger #1 is the co-enzymic-DNA-binding site required specifically for auto-PARP1-modification, the type of PARP1 enzymatic activity which is elevated in neoplastic cells. Zinc finger #1 is also the ATP-specific inhibitory site which suppresses auto-PARP1-modification in energetically competent (non-neoplastic) cells. Two-site inhibition strategies affords the potential to manipulate inhibition of PARP1 activity in a manner that may allow HAT-Pi treatment to more specifically target neoplastic tumor cells or other types of diseased cells, tissues and/or organs.

4. Modification of HAT-Pi Regimens for Non-Neoplastic Diseases or Conditions

HAT-Pi treatment regimens may be modified for the treatment of non-neoplastic diseases and conditions that may benefit from inhibition of the enzymatic activity of PARP1 and/or other ARP family enzymes, many of which have been implicated in a wide variety of diseases and conditions including, but not limited to:

Metabolic/genetic diseases or conditions, other than neoplastic disease, that may be caused or characterized by disregulation of PARP1 enzymatic activity and that may benefit from a HAT-Pi treatment regimen or modifications thereto;

Vector-based diseases and conditions that are potentially treatable using HAT-Pi include, but are not limited to those attributable to:

a) infectious disease vectors such as viruses, retro-viruses, bacteria, and parasites (single-cell and multi-cellular); and, b) non-living disease vectors such as asbestos, chemical toxins, or other.

DESCRIPTION OF FIGURES

FIG. 1. HAT inhibition of enzymatic activity of purified PARP1 in solution

Cloned human PARP-1 (8 nanomolar) was incubated with 100 nanomolar dA/dT, 50 micrograms/milliliter histone Hi and varying concentrations (50, 150, 450 micromolar) of $^{32}P$-$NAD^+$ in the absence and presence of inhibitor (50 micromolar) at physiological pH (7.3) as described (E. Kirsten, E. Kun, J. Mendeleyev, C. P. Ordahl, Methods in Molecular Biology 287 137 (2004) and Kun, 2004 op cit). Reactions were started by the addition of PARP-1 and incubated for 10 minutes at room temperature after which acid precipitable $^{32}P$ was determined. Results shown are the mean of triplicate determinations (SD±10%). A. Open squares, 3-aminobenzamide; B. Closed squares, bromodeoxyuridine (HAT); C. Closed circles, no inhibitor (control).

FIG. 2. HAT effects on neoplastic cell morphology and behavior

Calu6 and DU-145 cells were seeded at approximately $0.01 \times 10^6$ [ten thousand]cells per square centimeter and cultured in "plain medium" (Eagle's MEM with Earle's BBS medium, with added sodium pyruvate [0.11 milligrams/milliliter, final concentration], non-essential amino acids, and 10% fetal bovine serum). Both cell lines are 'adherent', meaning that they adhere to each other and to the culture dish surface and are retained during routine culture medium changes.

In half of the culture dishes plain medium was supplemented with 10 micromolar bromodeoxyuridine (HAT). After 14 days in culture all cultures were microscopically examined and photographed at the same magnification and the outlines of individual cells traced in representative fields. Cell nuclei, distinguishable inside cell outlines only in HAT-treated cultures, are shown in black. Arrows in panels B and D indicate examples of lamellipodia (open arrows) and cell-cell contact junctions (closed arrows).

Panel A, Calu-6 cells without HAT;
Panel B, Calu-6-cells with HAT;
Panel C, DU-145-cells without HAT;
Panel D, DU-145-cells with HAT.

Online information; Calu6 http://www(dot)atcc(dot)org/products/all/HTB-56(dot)aspx
Online information: DU-145 http://www(dot)atcc(dot)org/products/all/HTB-81(dot)aspx FIG. 3. Historic HAT-Pi treatment regimens Historic HAT-Pi Treatment Regimens Illustrated: Overview The HAT-Pi treatment regimens illustrated in panels A and B cover a period of 24 weeks (approximately 5 months) the duration of the most successful historic HAT-Pi treatment regimens reported. HAT was deliberately withdrawn during indicated intervals to allow for patient recovery from myelosuppression as determined by frequent hematology assessment. The regimen illustrated in A was adapted from a chart in the original publication (Calabresi, 1961 op cit, and references therein). The regimen illustrated in B was composed from text descriptions in publications of NCI-sponsored clinical trials (Kinsella, 1987 op cit; Chang, 1989 op cit; and references therein).

Panel A. HAT Bolus Infusions into the Circulation

Patient One (A.C.), a 65-year old woman with advanced metastatic melanoma, was the first historic patient to receive HAT-Pi treatment.

Drug Courses

HAT was administered as intravenous bolus injections 2-5 days per week. HAT dosages were reported in grams/kilogram body weight with the highest dose being 0.1 gram iododeoxyuridine per kilogram of patient body weight. (Assuming that Patient One was an individual weighing 60 kilograms (132 pounds) with a body surface area of 1.6 $M^2$, these values translate into daily infusions of approximately 3.75 grams (10.6 millimoles) HAT/$M^2$ of body surface area.) Two principal HAT courses were administered, the first course (#1) consisted of multiple infusions of increasing dosage over a period of about one month. The dosage was increased for a second course (#2) that was administered over a three week period.

Symptoms

At the outset of treatment, Patient One reported her subjective symptoms as "3.0" using a scale of 0-4, where 4 represents the maximum pain or discomfort imaginable. That symptom value dropped to 0.5 after 4 weeks of HAT infusion and remained low for approximately 4 weeks (PR #1; pain relief period number one) after withdrawal of HAT infusion. Return of increased symptoms (to 2.0) was followed by a second course of HAT treatment, followed in turn by a second decrease in symptoms, first to 1.0 and then again to 0.5. Unfortunately, HAT was not available at the time needed to provide this patient with a third course of HAT treatment and she succumbed to her disease.

Hematology

Blood samples were subjected hematology assessment twice weekly to monitor myelosuppression, which reached nadirs that marked the ends of each treatment period (nadirs #1 and #2) and which approximately coincide with the onset of periods of pain-relief (PR #1 and #2, respectively). HAT treatment resumption was contingent upon hematology values having returned to pre-established "normal" levels.

Tumors

Reduction in metastases and in the size of some tumors was noted during the course of HAT exposure but this was reversible and tumors and metastases recurred strongly after an extended period of (unintended) HAT withdrawal due to lack of drug availability.

Side-Effect

Alopecia was the only side effect charted for Patient One. It progressed to complete baldness within 13-weeks. The reversible nature of this side-effect is demonstrated by hair re-growth after week 20 which coincides with the extended period of (unintended) HAT withdrawal.

Panel B: Continuous Circulatory Infusion for 14-Days Alternating with 14-Day Infusion-Free Periods.

This panel illustrates the treatment courses given patients in NIH clinical trials itemized in Table 1 d-f.

Drug Courses

HAT was administered in repeated 14-day-long courses of continuous circulatory infusion (24 hours per day) administered by intravenous or intra-arterial routes. Each 14-day infusion course was followed by a 14-day infusion-free period.

Hematology

Blood tests were administered twice weekly during infusion and non-infusion periods. The typical timing of recovery of platelet numbers and marrow activity after nadirs was reported to be approximately seven to ten days after the last infusion day. In other words, patient blood cell counts typically returned to predetermined normal values several days to one week prior to the next scheduled infusion course.

FIG. 4. HAT chemical identities

HAT drugs are Halogenated Analogs of Thymidine because of their chemical structure. This figure illustrates some of the structural elements of thymidine that are similar to its halogenated analogs.

Panel A: Thymidine and its Structural Subunit Thymine

The methyl ($CH_3$) group in thymidine and thymine has a diameter of approximately 2.00 angstrom units, a distinctive characteristic that is mimicked by halogen atoms in HAT drugs.

Panel B: Iododeoxyuridine and its Structural Subunit Iodouracil

Iododeoxyuridine is structurally identical to thymidine except that the methyl group is replaced by an atom of iodine with a diameter of approximately 2.15 angstrom units.

Panel C: Bromodeoxyuridine and its Structural Subunit Bromouracil

Bromodeoxyuridine is structurally identical to thymidine except that the methyl group is replaced by an atom of bromine with a diameter of approximately 1.95 angstrom units.

Panel D: IPdR and its Metabolic Conversion

IPdR (5-iodo-2-pyrimidinone-2'-deoxyribose) is structurally identical to iododeoxyuridine except for the absence of an atom of oxygen. Ingested IPdR enters the liver where it is enzymatically converted to iododeoxyuridine by hepatic aldehyde oxidase.

FIG. 5. HAT-Pi treatment regimens

A full HAT-Pi treatment regimen takes place over a period of 24 weeks (top line of illustration). For each of the three regimens illustrated, HAT administration courses are interrupted by periods of no HAT administration (gap) for myelosuppression recovery. Periods of HAT administration, and intervening gaps along the 24 week time line vary according to method of delivery.

A. Circulatory Infusion

This panel illustrates HAT-Pi courses administered through continuous (24/7) circulatory infusion either by an intravenous or an intra-arterial route. Each HAT treatment cycle comprises 2-weeks of HAT administration followed by 2-weeks without HAT infusion.

B. Intraperitoneal Infusion

This panel illustrates HAT-Pi courses consisting of a 4-hour-long peritoneal infusions every day for 4 days, followed by a 2-week gap.

C. Oral Tablet (Potential)

This panel illustrates a potential regimen for administering HAT-Pi which has not been tested in human subjects. In this regimen, one treatment course consists of ingestion of IPdR tablets on one or more days, followed by a one-week gap. Parentheses indicate courses that have not been subjected to clinical evaluation.

In the foregoing specification, the present subject matter has been described with reference to specific exemplary embodiments thereof. It will, however, be evident that various modifications and changes may be made thereto without departing from the broader spirit and scope set forth in the appended claims. The specification and drawings are, accordingly, to be regarded in an illustrative sense rather than a restrictive sense.

The invention claimed is:

1. A method for treating pain caused by a neoplastic disease comprising:
   estimating a concentration of at least one halogenated analog of thymidine (HAT) required to produce and sustain at least a partial inhibition of poly (ADP-ribose) polymerase 1 (PARP-1) enzymatic activity in a live subject; and
   in an absence of any additional cell-kill or other chemotherapy or radiotherapy agents, administering the at least one halogenated analog of thymidine (HAT) in an amount sufficient to produce and sustain the estimated concentration in the blood of the live subject for at least as long as required to produce a subjective alleviation of pain in the subject.

2. The method of claim 1, wherein the at least one HAT comprises at least one of:
bromodeoxyuridine;
iododeoxyuridine;
at least one metabolite of bromodeoxyuridine;
at least one metabolite of iododeoxyuridine; and
at least one HAT pro-drug.

3. The method of claim 2, wherein the at least one HAT pro-drug comprises:
5-iodo-2-pyrimidinone-2'-deoxyribose.

4. The method of claim 1, wherein administering at least one HAT in an amount sufficient to produce and sustain the estimated concentration in the blood of the live subject comprises:
administering the at least one HAT to a subject in an amount sufficient to maintain a concentration of the at least one HAT of not less than 0.1 micromolar and not more than 100 micromolar in the circulating plasma of that subject.

5. The method of claim 4, wherein administering at least one HAT in an amount sufficient to maintain a plasma concentration of the at least one HAT in a subject of not less than 0.1 micromolar comprises infusion of:
said at least one HAT in a total daily dose not less than 0.1 gram per meter$^2$ of the subject's body surface and not more than 4.5 grams per meter$^2$ of the subject's body surface.

6. The method of claim 5, wherein administering said HAT comprises:
infusing said total daily dose at a constant rate over a 24-hour period; and
wherein infusing said total daily dose at a constant rate is maintained for successive 24-hour periods for at least as long as required to produce and maintain the subjective alleviation of pain in the subject.

7. The method of claim 6, wherein administering said HAT comprises dosing cycles of:
infusing said total daily dose over periods of at least four days and not more than 28 days followed by HAT-withdrawal for one or more weeks; and
repeating said dosing cycles, for at least as long as required to produce and maintain the subjective alleviation of pain in the subject.

8. The method of claim 5, wherein said infusing comprises at least one of:
intra-arterial (IA), intraperitoneal (IP) and intravenous (IV) infusion; and
injection into one of: a tumor mass, an associated anatomical space and an associated anatomical cavity.

9. The method of claim 3, wherein administering at least one HAT in an amount sufficient to produce and sustain the estimated concentration in the blood of the live subject comprises:
administering an oral dose of not less than 0.1 and not more than 2.4 grams per meter$^2$ of the subject's body surface of 5-iodo-2-pyrimidinone-2'-deoxyribose at least one time per day; and
repeating said daily dosing for periods of at least 4 days and repeating such dosing cycles, with suitable intervening periods of no HAT dosing, for at least as long as required to produce and maintain at least one of;
the subjective alleviation of symptoms in the subject; and
a detectable anti-tumor effect.

10. The method of claim 1, wherein administering at least one halogenated analog of thymidine (HAT) comprises:
administering said at least one HAT in an admixture with a diluent to form a pharmaceutical composition.

11. The method of claim 9, wherein the pharmaceutical composition contains a concentration in a range of approximately 0.5% to approximately 90% of said at least one HAT.

12. The method of claim 1, further comprising:
monitoring blood cell counts of the subject at predetermined intervals; and
suspending administration of said at least one HAT responsive to said blood cell counts dropping to a nadir predetermined for each of the blood cell counts.

13. The method of claim 12, further comprising:
responsive to suspending administration of said at least one HAT, resuming administration of said at least on HAT responsive to blood cell counts reaching predetermined acceptable levels.

14. The method of claim 1, further comprising:
responsive to development of any of a plurality of undesirable side effects, reducing the amount of the at least one HAT administered to a predetermined safe dose.

15. The method of claim 1, further comprising eliminating any subjects possessing reproductive potential as candidates for treatment of neoplastic disease by administration of at least one HAT.

16. The method of claim 1, wherein the neoplastic disease comprises cancer.

17. The method of claim 1, further comprising obtaining periodic quantitative symptom reports from said subject to gauge effectiveness of treatment with the at least one HAT.

18. A pharmaceutical composition for arresting human cancer cell replication and metastasis while inducing cancer cell senescence and death comprising at least one halogenated analog of thymidine (HAT) in a concentration effective to reduce pain from cancer.

19. The pharmaceutical composition of claim 18, further comprising a diluent.

20. A method for producing a sustained inhibition of poly (ADP-ribose) polymerase 1 (PARP-1) enzymatic activity in a subject comprising:
administering at least one PARP-1 inhibitor in an amount sufficient to produce and sustain a subjective alleviation of pain in the subject, the PARP-1 inhibitor comprising at least one halogenated analog of thymidine (HAT) in a concentration in the subject of not less than 0.1 micromolar.

* * * * *